(12) United States Patent
Bachawala et al.

(10) Patent No.: US 11,484,857 B2
(45) Date of Patent: *Nov. 1, 2022

(54) ENVIRONMENTALLY BIODEGRADABLE MICROCAPSULES

(71) Applicant: TruCapsol LLC, Allentown, PA (US)

(72) Inventors: Praveen Bachawala, Allentown, PA (US); Jiten Odhavji Dihora, Center Valley, PA (US)

(73) Assignee: TRUCAPSOL LLC, Allentown, PA (US)

( * ) Notice: Subject to any disclaimer, the term of this patent is extended or adjusted under 35 U.S.C. 154(b) by 59 days.

This patent is subject to a terminal disclaimer.

(21) Appl. No.: 16/776,965

(22) Filed: Jan. 30, 2020

(65) Prior Publication Data

US 2021/0237020 A1 Aug. 5, 2021

Related U.S. Application Data

(63) Continuation of application No. 16/776,828, filed on Jan. 30, 2020.

(51) Int. Cl.
| | | |
|---|---|---|
| *B01J 13/16* | (2006.01) | |
| *C08K 5/17* | (2006.01) | |
| *C08G 18/28* | (2006.01) | |
| *C08G 18/58* | (2006.01) | |
| *A61K 8/11* | (2006.01) | |
| *A61Q 5/02* | (2006.01) | |
| *A61Q 5/12* | (2006.01) | |
| *A61Q 15/00* | (2006.01) | |
| *A61Q 19/00* | (2006.01) | |
| *A61Q 19/10* | (2006.01) | |
| *B01J 13/14* | (2006.01) | |
| *C11B 9/00* | (2006.01) | |
| *C11D 3/00* | (2006.01) | |
| *C11D 3/50* | (2006.01) | |
| *C08L 1/02* | (2006.01) | |
| *C08F 222/06* | (2006.01) | |

(52) U.S. Cl.
CPC ............. *B01J 13/16* (2013.01); *A61K 8/11* (2013.01); *A61Q 5/02* (2013.01); *A61Q 5/12* (2013.01); *A61Q 15/00* (2013.01); *A61Q 19/007* (2013.01); *A61Q 19/10* (2013.01); *B01J 13/14* (2013.01); *C08G 18/289* (2013.01); *C08G 18/581* (2013.01); *C08K 5/17* (2013.01); *C11B 9/00* (2013.01); *C11D 3/001* (2013.01); *C11D 3/505* (2013.01); *C08F 222/06* (2013.01); *C08L 1/02* (2013.01)

(58) Field of Classification Search
CPC .. B01J 13/16; B01J 13/14; A61K 8/11; A61K 2800/412; A61K 8/87; A61Q 5/02; A61Q 5/12; A61Q 15/00; A61Q 19/007; A61Q 19/01; A61Q 13/00; C08G 18/289; C08G 18/581; C08G 2230/00; C08G 18/003; C08G 18/3225; C08G 59/188; C08G 18/792; C08K 5/17; C11B 9/00; C11D 3/001; C11D 3/505; C11D 17/0039; C08F 222/06; C08L 1/02; C08L 3/02; C08L 1/284; C08L 3/08; C08L 5/08; F28D 20/023; A23L 27/72
See application file for complete search history.

(56) References Cited

U.S. PATENT DOCUMENTS

| | | | |
|---|---|---|---|
| 3,345,358 | A | 10/1967 | Inklaar |
| 3,819,838 | A | 6/1974 | Smith et al. |
| 3,870,542 | A * | 3/1975 | Ida .................. B01J 13/025 8/526 |
| 4,076,774 | A | 2/1978 | Short |
| 4,626,471 | A * | 12/1986 | Chao ................ B01J 13/185 503/214 |
| 5,227,446 | A | 7/1993 | Denzinger et al. |
| 5,550,189 | A | 8/1996 | Qin et al. |
| 5,574,179 | A | 11/1996 | Wahl et al. |
| 5,601,760 | A | 2/1997 | Rosenberg |
| 5,837,747 | A | 11/1998 | Soon-Shiong et al. |
| 6,248,909 | B1 | 6/2001 | Akimoto et al. |

(Continued)

FOREIGN PATENT DOCUMENTS

| | | |
|---|---|---|
| CA | 1049335 A | 2/1979 |
| EP | 0815743 A2 | 1/1998 |

(Continued)

OTHER PUBLICATIONS

Tmakova et al. (2016). Plant-derived surfactants as an alternative to synthetic surfactants: surface and antioxidant activities. Chemical Papers, 70(2), 188-196.
U.S. Appl. No. 16/287,509, filed Feb. 27, 2019.
Adhesives Magazine (2016). SARTOMER: Acrylate Oliogmer Available at: https://www.adhesivesmag.com/articles/94922-sartomer-acrylate-oligomer.
Leung et al. (2017). Enteric coating of micron-size drug particles through a Wurster fluid-bed process. Powder Technology, 317, 247-252.
Luo et al. (2014). Zein-based micro-and nano-particles for drug and nutrient delivery: A review. Journal of Applied Polymer Science, 131(16): 40696, 1-12.

(Continued)

*Primary Examiner* — Irina S Zemel
(74) *Attorney, Agent, or Firm* — Caesar Rivise, PC

(57) ABSTRACT

Disclosed is a composition including controlled release particles, wherein each of the controlled release particles includes: (a) a core including at least one hydrophobic active ingredient; and (b) a wall at least partially surrounding the core and including the reaction products of: (i) an organofunctional silane; (ii) an epoxy; (iii) an amine; (iv) an isocyanate; (v) an epoxide curing agent; wherein the controlled release particles are effective to retain the at least one hydrophobic active ingredient upon exposure to water and effective to release the at least one hydrophobic active ingredient in response to friction. A method for preparing the composition is also disclosed.

28 Claims, 16 Drawing Sheets

(56) References Cited

U.S. PATENT DOCUMENTS

| | | | |
|---|---|---|---|
| 6,465,016 | B2 | 10/2002 | Parikh et al. |
| 6,572,919 | B2 | 6/2003 | Westland et al. |
| 6,596,073 | B1 | 7/2003 | Nyssen et al. |
| 6,855,335 | B2 | 2/2005 | Seok et al. |
| 7,431,986 | B2 | 10/2008 | Van Lengerich et al. |
| 8,900,495 | B2 | 12/2014 | Pacorel et al. |
| 9,205,395 | B2 | 12/2015 | Yan |
| 9,332,774 | B2 | 5/2016 | Nakhasi et al. |
| 9,427,719 | B2 | 8/2016 | Viaud-Massuard et al. |
| 9,714,397 | B2 | 7/2017 | Feng et al. |
| 9,937,477 | B2 | 4/2018 | Zhang et al. |
| 9,944,886 | B2 | 4/2018 | Hitchcock et al. |
| 9,993,401 | B2 | 6/2018 | Barnett et al. |
| 10,188,593 | B2 | 1/2019 | Dihora et al. |
| 11,179,302 | B2 | 11/2021 | Dardelle |
| 11,344,502 | B1 | 5/2022 | Dihora et al. |
| 2004/0017017 | A1 | 1/2004 | Van Lengerich et al. |
| 2004/0033264 | A1 | 2/2004 | Sawhney |
| 2005/0272628 | A1 | 12/2005 | Meli et al. |
| 2005/0276831 | A1 | 12/2005 | Dihora et al. |
| 2008/0085297 | A1 | 4/2008 | Dave et al. |
| 2008/0103265 | A1 | 5/2008 | Schocker et al. |
| 2008/0167188 | A1 | 7/2008 | Fischer et al. |
| 2009/0209661 | A1 | 8/2009 | Somerville Roberts et al. |
| 2010/0011610 | A1 | 1/2010 | Bittorf et al. |
| 2010/0028451 | A1 | 2/2010 | Kaplan et al. |
| 2011/0052680 | A1 | 3/2011 | Hendrickson et al. |
| 2011/0268778 | A1 | 11/2011 | Dihiora et al. |
| 2011/0268802 | A1 | 11/2011 | Dihora et al. |
| 2012/0128752 | A1 | 5/2012 | Loo et al. |
| 2013/0004617 | A1 | 1/2013 | Zhang et al. |
| 2013/0022654 | A1 | 1/2013 | Deshmukh et al. |
| 2013/0084379 | A1 | 4/2013 | Gregson et al. |
| 2013/0239429 | A1 | 9/2013 | Vella et al. |
| 2014/0199244 | A1 | 7/2014 | Rijcken et al. |
| 2014/0335032 | A1 | 11/2014 | Panandiker et al. |
| 2015/0252312 | A1 | 9/2015 | De Villeneuve et al. |
| 2016/0038428 | A1 | 2/2016 | Harel et al. |
| 2016/0128944 | A1 | 5/2016 | Chawrai et al. |
| 2016/0158121 | A1 | 6/2016 | Lei et al. |
| 2016/0166480 | A1 | 6/2016 | Lei et al. |
| 2016/0206561 | A1 | 7/2016 | Kohane et al. |
| 2016/0228338 | A9 | 8/2016 | Dihora et al. |
| 2017/0165627 | A1 | 6/2017 | Duan et al. |
| 2018/0015009 | A1 | 1/2018 | Soubiran et al. |
| 2018/0042825 | A1 | 2/2018 | Lei et al. |
| 2019/0275490 | A1 | 9/2019 | Bachawala |
| 2021/0045409 | A1 | 2/2021 | Witteveen et al. |
| 2021/0237018 | A1 | 8/2021 | Bachawala et al. |
| 2021/0237019 | A1 | 8/2021 | Bachawala et al. |
| 2022/0133603 | A1 | 5/2022 | Bachawala et al. |

FOREIGN PATENT DOCUMENTS

| | | | | |
|---|---|---|---|---|
| EP | 1371410 | A1 | 12/2003 | |
| EP | 1797946 | A2 | 6/2007 | |
| WO | 9901214 | A1 | 1/1999 | |
| WO | 0105926 | A1 | 1/2001 | |
| WO | 03013538 | A1 | 2/2003 | |
| WO | 2004064971 | A2 | 8/2004 | |
| WO | 2006024411 | A2 | 3/2006 | |
| WO | 2007135583 | A2 | 11/2007 | |
| WO | 2008118133 | A2 | 10/2008 | |
| WO | 2009098226 | A1 | 8/2009 | |
| WO | 2011041395 | A2 | 4/2011 | |
| WO | WO-2015091877 | A1 * | 6/2015 | ............. A01N 25/08 |
| WO | 2016071151 | A1 | 5/2016 | |
| WO | 2017023830 | A1 | 2/2017 | |
| WO | 2020195132 | A1 | 10/2020 | |

OTHER PUBLICATIONS

Silverajah et al. (2012). Mechanical, thermal and morphological properties of poly (lactic acid)/epoxidized palm olein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

English language abstract for WO 2020195132 A1 (2020).

http://polymerdatabase.com/polymer%20physics/sigma.html downloaded on Apr. 29, 2022.

Ko et al., "Characterization of hydrophilic-hydrophobic polymeric surfaces by contact angle measurements", Journal of Colloid and Interface Science, vol. 82(1) (1981).

OECD 301D method (OECD 1992, Test No. 301 Ready Biodegradability, OECD Guidelines for the Testing of Chemicals, Section 3, OECD Publishing, Paris, https://doi.org/10.1787/9789264070349-en.

Thakore et al. (2001). "Studies on biodegradability, morphology and thermo-mechanical properties of LDPE/modified starch blends." European polymer journal, 37(1), 151-160.

U.S. Appl. No. 16/682,862, filed Nov. 13, 2019.
U.S. Appl. No. 16/830,152, filed Mar. 25, 2020.
U.S. Appl. No. 16/853,003, filed Apr. 20, 2020.
U.S. Appl. No. 17/517,816, filed Nov. 3, 2021.
U.S. Appl. No. 16/776,828, filed Jan. 30, 2020.
U.S. Appl. No. 16/777,048, filed Jan. 30, 2020.
U.S. Appl. No. 17/724,141, filed Apr. 19, 2022.
U.S. Appl. No. 17/724,166, filed Apr. 19, 2022.
U.S. Appl. No. 17/848,345, filed Jun. 23, 2022.
U.S. Appl. No. 17/861,204, filed Jul. 9, 2022.

* cited by examiner

Type A Particle

Type B Particle – Sealing the Pores

Type C Particle – Alkaline Conditions

ENVIRONMENTALLY BIODEGRADABLE MICROCAPSULES

CROSS-REFERENCE TO RELATED APPLICATIONS

This application is a continuation of U.S. application Ser. No. 16/776,828, filed on Jan. 30, 2020, the entire contents of all of which are incorporated herein by reference.

FIELD OF THE INVENTION

This invention relates to controlled release compositions, encapsulation compositions and methods for making and using them.

DESCRIPTION OF RELATED ART

There are many microencapsulated delivery systems disclosed in the art to control the release of the encapsulated active or provide release when a specific trigger is applied. Such systems have previously suffered from a number of drawbacks.

Controlled release microcapsules that provide release of active upon application of shear or friction generally suffer from several drawbacks: (1) such microcapsules are made of highly crosslinked membranes and membrane materials that cannot be broken down by microbes found in the environment, (2) despite such highly crosslinked membranes, the materials of construction of the membrane impart high permeabilities when incorporated into products that contain high levels of surfactant, solvents, and/or water, which results in the premature benefit agent release, (3) they can only effectively encapsulate a limited breadth of benefit agents, (4) they either are so stable that they do not release the benefit agent in use or have insufficient mechanical stability to withstand the processes required to incorporate them in and/or make a consumer product, (5) they do not adequately deposit on the surface that is being treated with consumer product that contains microcapsules, and/or (6) they do not comprise membrane materials that have a favorable environmental degradability profile.

Such microcapsules are made via chemical processes that require the development of a membrane at the oil-water interface. Said membrane can be developed from the oil side or the water side, or both. An emulsion comprising the active material (dispersed phase) is stabilized in a continuous phase. In one mode, a shell material is deposited from the continuous phase onto a dispersed phase via precipitation of the shell material. In another mode, the shell material is manufactured within the dispersed phase, and migration of the shell material is induced via an interfacial reaction or insolubility of the shell material in the oil phase. The two approaches could be combined to develop "multi-shell" capsules.

The permeability and the solubility parameter of the membrane determines the likelihood and the rate of diffusion of the encapsulated active out of the microcapsule. The solubility parameter of the membrane is determined by the choice of monomers that are reacted to form the shell material at the interface. One means to influence the solubility parameter is to build a hybrid inorganic/organic membrane at the oil-water interface. An organic hydrophobic active will have little to no solubility in an inorganic shell material; therefore, one can reduce the diffusion of the core material. The continuing challenge is in finding ways to build a hybrid membrane because inorganic and organic materials are incompatible.

While others have attempted to improve the barrier properties of microcapsules, there remains significant shortcoming and limitations in the art. For example, U.S. Pat. No. 9,944,886B2 Hitchcock et. al. describes metal coated microcapsules with improved barrier properties. The Hitchcock metal coating is developed after the formation of the microcapsule membrane, via the use of sterically stabilized nanosuspension of metal particle. Such metal coated microcapsules could improve barrier properties; however, it is difficult to imagine how the encapsulated active would be released, since a metal coating would be difficult to fracture. Furthermore, the processing steps involved to achieve the metal coating are laborious and expensive. Moreover, such metal coating could render the microcapsules non-environmentally biodegradable.

Because of these drawbacks, a preferable means is to develop an inorganic membrane that would reside near the hydrophobic active material, so that the active material has low propensity to diffuse into this inorganic layer and leak out of the membrane. A preferable means is to incorporate materials that would diffuse to the oil-water interface, react at the interface to seal the pores, thereby providing additional barrier properties to the established membrane.

Chemical processes utilized to manufacture controlled release microcapsules generally utilize thermal initiators—either in the aqueous phase or the lipophilic phase. High crosslink density of the shell material can be achieved at higher temperatures, for two reasons. First, there is a higher reactivity of the monomers at high temperature. Second, as the monomers react, the resulting polymer has a higher glass transition temperature. A higher reaction temperature results in higher mobility of the crosslinked polymer, providing a means to achieve a higher reactivity of the monomers to achieve a higher crosslink density. However, processing actives at higher temperatures can result in loss of the active, via evaporation or via thermal degradation. At low temperatures, such thermally initiated reactions require long batch cycle times (generally more than 24 hours), thus increasing the cost of the capsules. Instead, it is desired to complete these chemical reactions at lower temperatures in order to reduce the loss of volatile actives, and simultaneously achieve a degree of crosslinking that is sufficient to reduce the diffusion of the encapsulated active out of the microcapsule, in a time that does not significantly increase the cost of the microcapsules, and simultaneously maintains an environmental biodegradability of the polymer above 50%.

U.S. Pat. No. 9,937,477B2 Zhang et. al. discloses core/shell microcapsules that are manufacture using free radical polymerization of acrylates; such microcapsules require multi-step reactions that require heating the capsules to 95 degrees Centigrade for up to 6 hours. It is well known that such polyacrylate capsules that are highly crosslinked have poor environmental biodegradability.

US20170165627A1 Duan et. al. provides seed microcapsules made via free radical polymerization. Duan incorporates additional initiator to further "coat" the capsules. In this way, the existing membrane's crosslink density is increased; however, no other ingredients are added to form this additional coating. The additional initiator added acts to achieve a highly crosslinked membrane that completes the acrylate polymerization both from the oil phase as well as the water phase.

US2018/0015009A1 Soubiran et. al. provides microcapsules manufactured via interfacial polymerization utilizing isocyanate and polyethyeleneimine that are prepared at temperatures less than 85 degrees Centigrade. Soubiran also mention the use of additional copolymers that can coat the microcapsules; however, such coating is not covalently bound to the microcapsule membrane materials (since Soubiran claims that such coating material can be added to the microcapsule slurry or the shampoo formulation). Moreover, Soubiran does not contemplate a hybrid inorganic/organic shell to reduce the diffusion of the encapsulated active.

Conventional controlled release particles that comprise a core and a shell have several limitations. First, such capsules prematurely release the active material when suspended in a finished product formulation, such as cleaning product formulations. Second, such capsules have poor environmental biodegradability due to the nature of materials used and the degree of crosslinking that is achieved in order to reduce the diffusion of the active. Third, it is difficult to control the release profile of the encapsulated active. Fourth, poor adhesion of particles to the substrate result in significant loss of the particles, especially when formulations containing such particles are used in rinse-off applications.

There is a challenge in designing a membrane that minimizes the diffusion of the encapsulated active into the surrounding formulation, and yet is environmentally biodegradable. Environmentally biodegradable polymers generally swell in water or are soluble in water. In contrast, microcapsule membranes generally need to resist swelling or dissolution in aqueous cleaning product formulation. A high degree of crosslinking within the membrane can reduce swelling and solubility; however, such highly crosslinked membranes are difficult for environmentally available microbes to digest and breakdown. Accordingly, it is desired to provide microcapsules that have lower permeability, yet good environmental biodegradability.

It is further desired to improve the adhesion of particles to substrates in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water.

It is further desired to remove soil and dirt, but desired to retain active materials during the rinsing process by the retention of microcapsules on the substrate.

It is further desired to provide a means to manipulate the release profile of the encapsulated active.

It is further desired to provide microcapsules that are processed at temperatures at or below 60° C., with a batch cycle time of less than 12 hours, and able to achieve a degree of crosslinking that is sufficient to reduce the diffusion of the encapsulated active out of the microcapsule yet provide more than 50% environmental biodegradability of the membrane material.

US2011/0268778A1 Dihora et. al. provides microcapsules made using UV initiation in order to form membranes at lower temperatures. However, prior to the free radical polymerization to form the membrane, the hydrophobic active material needs to be heated to temperatures beyond 60 degrees Centigrade. Moreover, Example 2 of the application clearly delineates poorer barrier properties of the membrane made via UV initiator versus the same capsules made via use of thermal initiation. Because of the non-transparency of the system, UV initiation to form a membrane has low efficiency. The resulting barrier properties and biodegradability of the resulting polyacrylate microcapsules are poor.

Hence, it is desired to provide low permeability microcapsules that are able to retain the encapsulated active in surfactant containing solutions, or under highly dilute aqueous conditions. It is desired to improve the adhesion of microcapsules onto the desired substrate during rinse-off applications. It is desired to release the encapsulated active in larger quantities, and over a longer duration of time. It is desired to have capsules that have a favorable environmental biodegradability profile as defined by OECD 301D method (OECD 1992, Test No. 301 Ready Biodegradability, OECD Guidelines for the Testing of Chemicals, Section 3, OECD Publishing, Paris, https://doi.org/10.1787/9789264070349-en).

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

The present invention relates to microcapsules comprising a hybrid inorganic/organic membrane developed around the core material to reduce the diffusion of core material into the environment and alternative materials and methods are presented to seal the pores in the membrane while also improving environmental biodegradability.

The present invention relates to three types of particles. Type A particles have the basic framework of the microcapsules that provide a hybrid inorganic/organic membrane surrounding a core material; Type B particles are provided by adjustment of the pH of the suspension into the acidic region (less than 7) followed by incorporation of additional reactants that provide better barrier properties and better environmental biodegradability; Type C particles are provided by adjustment of the pH of the suspension into the alkaline region (greater than 7) followed by incorporation of additional reactants that provide better barrier properties and better environmental biodegradability. Type B particles are preferably suited for low pH cleaning product formulations (e.g. liquid fabric softener). Type C particles are better suited for high pH cleaning product formulations (e.g. liquid detergents).

A first aspect of the invention is a composition comprising controlled release particles Type A, wherein each of the controlled release particles comprises:
(a) a core comprising at least one hydrophobic active ingredient; and
(b) a membrane surrounding the core and comprising the reaction product of:
  an epoxy;
  an epoxide curing agent;
  an amine; and
  an isocyanate,
  an organofunctional silane;
  optionally, an inorganic solid particle;
  optionally, a natural polysaccharide;
  optionally, a plasticizer
  optionally, a copolymer of maleic anhydride
wherein the controlled release particles are effective to retain the at least one hydrophobic active ingredient upon exposure to water and effective to release the at least one hydrophobic active ingredient in response to friction.

A second aspect of the invention is a composition comprising controlled release particles Type B, wherein each of the controlled release particles comprises:

(a) a core comprising at least one hydrophobic active ingredient; and (b) a wall at least partially surrounding the core and comprising the reaction product of:
- an epoxy;
- an epoxide curing agent;
- an amine; and
- an isocyanate,
- an organofunctional silane;
- a copolymer of maleic anhydride;
- a polyaziridine;
- optionally, an inorganic solid particle;
- optionally, a natural or modified polysaccharide;
- optionally, a plasticizer;
- optionally, a polyoxazoline
- optionally, a carbodiimide wherein the controlled release particles are effective to retain the at least one hydrophobic active ingredient upon exposure to water and effective to release the at least one hydrophobic active ingredient in response to friction.

A third aspect of the invention is a composition comprising controlled release particles Type C, wherein each of the controlled release particles comprises:

(a) a core comprising at least one hydrophobic active ingredient; and (b) a wall at least partially surrounding the core and comprising the reaction product of:
- an epoxy;
- an epoxide curing agent;
- an amine; and
- an isocyanate,
- an organofunctional silane;
- a copolymer of maleic anhydride;
- a carboxy containing polysaccharide or cellulose;
- a polyfunctional linker;
- optionally, an inorganic solid particle;
- optionally, a natural polysaccharide;
- optionally, a plasticizer wherein the controlled release particles are effective to retain the at least one hydrophobic active ingredient upon exposure to water and effective to release the at least one hydrophobic active ingredient in response to friction.

In certain embodiments, the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the organofunctional silane as at least one member selected from the group consisting of alkoxylated silane, trialkoxy silanes, functionalized trialkoxysilanes (amino, glycidoxy, methacryloxy, vinyl), tetraalkoxylated silanes including tetramethoxy silane and tetraethoxy silane, 1,2-bis(triethyxysilyl)ethane.

In certain embodiments the epoxy is at least one member selected from the group consisting of epoxidized unsaturated oils such as epoxidized soybean oil, epoxidized vegetable oil, and the like; epoxidized alcohols such as isoborbide glycidyl ether, polyglycerol-3-glycidyl ether, castor oil glycidyl ether; epoxidized polysaccharides such as sorbitol polyglycidyl ether.

In certain embodiments, the amine is at least one member selected from the group consisting of linear aliphatic amines, aromatic amines, silicone amines, branched amines, polyamines, polyetheramines, and amino acids.

In certain embodiments, the isocyanate is at least one member selected from the group consisting of aliphatic isocyanates, aromatic isocyanates, polymeric isocyanates containing more than 3 isocyanate functionalities, cyclic isocyanates, hydrophilic isocyanates, hydrophobic isocyanates, waterborne isocyanates and urethane acrylates containing isocyanate functionalities.

In certain embodiments, the inorganic solid particles comprise organically modified or water insoluble clays, minerals, salts. Said inorganic solid particles preferably comprise talc, calcium carbonate, bentonite.

In certain embodiments, the copolymer of maleic anhydride comprises the reaction products of dehydrated maleic acid with acyclic or cyclic or vinylic aromatic alkenes. Preferably, the copolymers of maleic anhydride are neutral or alkaline water-soluble copolymers of isobutylene or ethylene or alkylene and maleic anhydride that may be in the form of an amide ammonium salt.

In certain embodiments, the polysaccharide comprises natural polysaccharides or modified polysaccharides. Natural polysaccharides include natural starches such as tapioca, potato, corn, rice, wheat, and the like. Modified polysaccharides comprise carboxy modified polysaccharide or cellulose such as carboxymethyl starch, carboxymethyl chitosan, chitosan oligosaccharide, hydroxy propyl methyl starch, hydroxy propyl cellulose, ethyl cellulose, methyl cellulose, and octenyl succinic anhydride modified starch.

In certain embodiments, the polyaziridine comprises a polymer with more than one aziridine functionality. The aziridine can be present as terminal groups of a monomer or oligomer. The aziridine may be pendant groups attached to a polymer backbone. Aziridine is also known as azacyclopropane, ethylene imine, aminoethylene, azirane, dimethyleneimine, dimethylenimine, and ethylimine In certain embodiments, the polyoxazoline comprise a polymer with more than one oxazoline functional groups. The oxazolines can be present as the terminal end of a polymer or can be pendant groups attached to a polymer backbone. The oxazolines may be product of free radical polymerization of vinyl oxazolines. Oxazolines are also known as oxazaolyls.

In certain embodiments, the plasticizers are polymeric in nature, having a molecular weight greater than 1000 Daltons, and are preferably methyl esters of rosin, polyazelate esters, di-fatty acid esters, citrate esters, polyadipate esters, and polyester resins consisting of inner and intra-esters of polyhydroxy carboxylic acids.

In certain embodiments, the polyfunctional linker comprises a monomer or polymer having at least 2 functional groups that are capable of reacting with carboxylate groups. The functional groups are preferably terminal or pendant groups. The polyfunctional linker comprises materials selected from the group consisting of both aliphatic dihaloalkanes such as 1,3-dibromopropane, 1,4-dibromobutane, 1,5-dibromopentane, 1,6-dibromhexane, 1,7-dibromoheptane, and cyclic comprising dibromo isomers of cyclobutene, cyclopentane, cyclohexane, cyclooctane; diepoxides such as 1,4-butanediol diglycidyl ether and diepoxybutane, diepoxides of both unstaturated and hydrogenated bisphenol A; polyfunctional epoxides such as castor oil glycidyl ether, epoxidized soybean oil, and the like.

In certain embodiments, the epoxide curing agent is at least one member selected from the group consisting of curing agents having 2 or more epoxy functional groups which are terminally located. Suitable materials include trimethylol propane triglycidyl ether, resins containing acrylate and epoxy functional groups, diepoxide of the cycloapliphatic alcohol, hydrogenated Bisphenol A, resorcinol/bisphenol F resin with polyfunctional epoxide resin blend.

In certain embodiments, the carbodiimide is at least one member selected from the group consisting of waterborne polycarbodiimide resin, copolymer containing carbodiimide and isocyanate functionalities, copolymer containing carbodiimide and epoxy functionalities, ethyl carbodiimide hydrochloride.

In certain embodiments, the controlled release particles have a diameter from 0.1 microns to less than 200 microns.

In certain embodiments, the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

In certain embodiments, the composition further comprises at least one suspension agent to suspend the controlled release particles, wherein the at least one suspension agent is at least one member selected from the group consisting of a rheology modifier, a structurant and a thickener.

In certain embodiments, the at least one suspension agent has a high shear viscosity at, 20 sec$^{-1}$ shear rate and at 21° C., of from 1 to 7000 cps and a low shear viscosity, at 0.5 sec$^{-1}$ shear rate at 21° C., of greater than 1000 cps.

In certain embodiments, the composition is a fluid having a high shear viscosity, at 20 sec$^{-1}$ and at 21° C., of from 50 to 3000 cps and a low shear viscosity, at 0.5 sec$^{-1}$ shear rate at 21° C., of greater than 1000 cps.

In certain embodiments, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax, modified celluloses, and mixtures thereof.

In certain embodiments, the composition comprises two different controlled release particles selected from the group consisting of friction-triggered release microcapsules which release the encapsulated active material at different rates due to the different in the viscosity of the core material.

In certain embodiments, the composition comprises two different controlled release particles selected from the group consisting of friction-triggered release microcapsules and water-triggered release microcapsules.

In certain embodiments, the at least one hydrophobic active ingredient comprises a mixture of a hydrophobic active and a material selected from the group consisting of brominated oils, epoxidized oils, highly nonpolar oils, hydrophobically modified inorganic particles, nonionic emulsifiers, oil thickening agents.

In certain embodiments, the composition has an Environmental Biodegradability greater than 50%.

A fourth aspect of the invention is a method for preparing Type A particles of the composition of the invention, said method comprising the steps of:
(a) preparing an oil phase comprising the at least one hydrophobic active ingredient, at least one isocyanate, at least one epoxy, at least one organofunctional silane, and at least one epoxide curing agent, optionally a polysaccharide, optionally a plasticizer; and optionally an inorganic solid particle;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) adding an amine moiety containing material to react with the at least one isocyanate, or the one epoxy, or the one organofunctional silane for about 0.5 hours at room temperature to provide a barrier;
(e) increasing a temperature to 60° C. and reacting for 2 to 5 hours;
(f) cooling the suspension to room temperature and adding structuring agents to the suspension of the controlled release particles to homogeneously suspend the particles in an aqueous dispersion.

A fifth aspect of the invention is a method for preparing Type B particles of the composition of the invention, said method comprising the steps of:
(a) preparing an oil phase comprising the at least one hydrophobic active ingredient, at least one isocyanate, at least one epoxy, at least one organofunctional silane, and at least one epoxide curing agent, at least one polyaziridine, optionally a polysaccharide, optionally a plasticizer; and optionally an inorganic solid particle;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) adding an amine moiety containing material to react with the at least one isocyanate, or the one epoxy, or the one organofunctional silane for about 0.5 hours at room temperature to provide a barrier;
(e) adding the copolymer of maleic anhydride, predissolved in water and allow it to react with contents of suspension for 1 hr;
(f) acidifying the contents of the mixture by adding dilute hydrochloric acid or citric acid;
(g) optionally, adding acidified carboxy functional polysaccharide or cellulose to the mixture;
(h) optionally, adding a fresh aliquot of polyaziridine or polyoxazoline to enable crosslinking of the two free acids;
(i) optionally, adding a carbodiimide to the suspension
(j) increasing a temperature to 60° C. and reacting for 2 to 5 hours;
(k) Cooling the suspension to room temperature and adding structuring agents to the suspension of the controlled release particles to homogeneously suspend the particles in an aqueous dispersion.

A sixth aspect of the invention is a method for preparing Type C particles of the composition of the invention, said method comprising the steps of:
(a) preparing an oil phase comprising the at least one hydrophobic active ingredient, at least one isocyanate, at least one epoxy, at least one organofunctional silane, and at least one epoxide curing agent, optionally a polysaccharide, optionally a plasticizer; and optionally an inorganic solid particle;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;

(d) adding an amine moiety containing material to react with the at least one isocyanate, or the one epoxy, or the one organofunctional silane for about 0.5 hours at room temperature to provide a barrier;

(e) adding the copolymer of maleic anhydride, pre-dissolved in water and allow it to react with contents of suspension for 1 hr.

(f) adding the carboxy functional polysaccharide or cellulose to the mixture (g) increasing the pH of the suspension by using sodium hydroxide to achieve carboxylate anionic groups at the surface of the capsule; adding a polyfunctional linker to react with the carboxylate functionality from both the copolymer of maleic anhydride and modified polysaccharide or modified cellulose;

(h) increasing a temperature to 60° C. and reacting for 2 to 5 hours;

(i) Coiling the suspension to room temperature and adding structuring agents to the suspension of the controlled release particles to homogeneously suspend the particles in an aqueous dispersion.

In certain embodiments of the method, the oil phase comprises the at least one epoxide curing agent and the at least one organofunctional silane.

In certain embodiments of the method, the emulsifier is a member selected from the group consisting of palmitamidopropyltrimonium chloride, distearyl dimonium chloride, cetyltrimethy lammonium chloride, quaternary ammonium compounds, fatty amines, aliphatic ammonium halides, alkyldimethyl benzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethylaminoethyl methacrylate), poly(acrylamide-co-diallyldimethylammonium chloride), polybis(2-chloroethyl)ether-alt-1,3-bis(3-(dimethylamino)propylurea quaternized, polyalkylene glycol ether, polyvinyl acetate, copolymers of polyvinyl acetate, polyacrylamide, poly(N-isopropylacrylamide), poly (2-hydroxypropyl methacrylate), poly(-ethyl-2-oxazoline), poly (2-isopropenyl-2-oxazoline-co-methyl methacrylate), poly (methyl vinyl ether), and polyvinyl alcohol-co-ethylene), polyvinyl pyrrolidone, copolymers of polyvinhyl pyrrolidone, 1H-Imidazolium, 1-ethenyl-3-methyl-, chloride, polymer with 1-ethenyl-2-pyrrolidinone, vinyl acetate and gum arabic.

BRIEF DESCRIPTION OF SEVERAL VIEWS OF THE DRAWINGS

The invention will be described in conjunction with the following drawings, wherein:

FIG. 8 shows areas (arrow 8) where aziridine in the oil phase, has reacted with modified polysaccharide in the aqueous phase, through the pores in the membrane, in effect sealing the pores.

DETAILED DESCRIPTION OF PREFERRED EMBODIMENTS OF THE INVENTION

Glossary

Figure 1A:
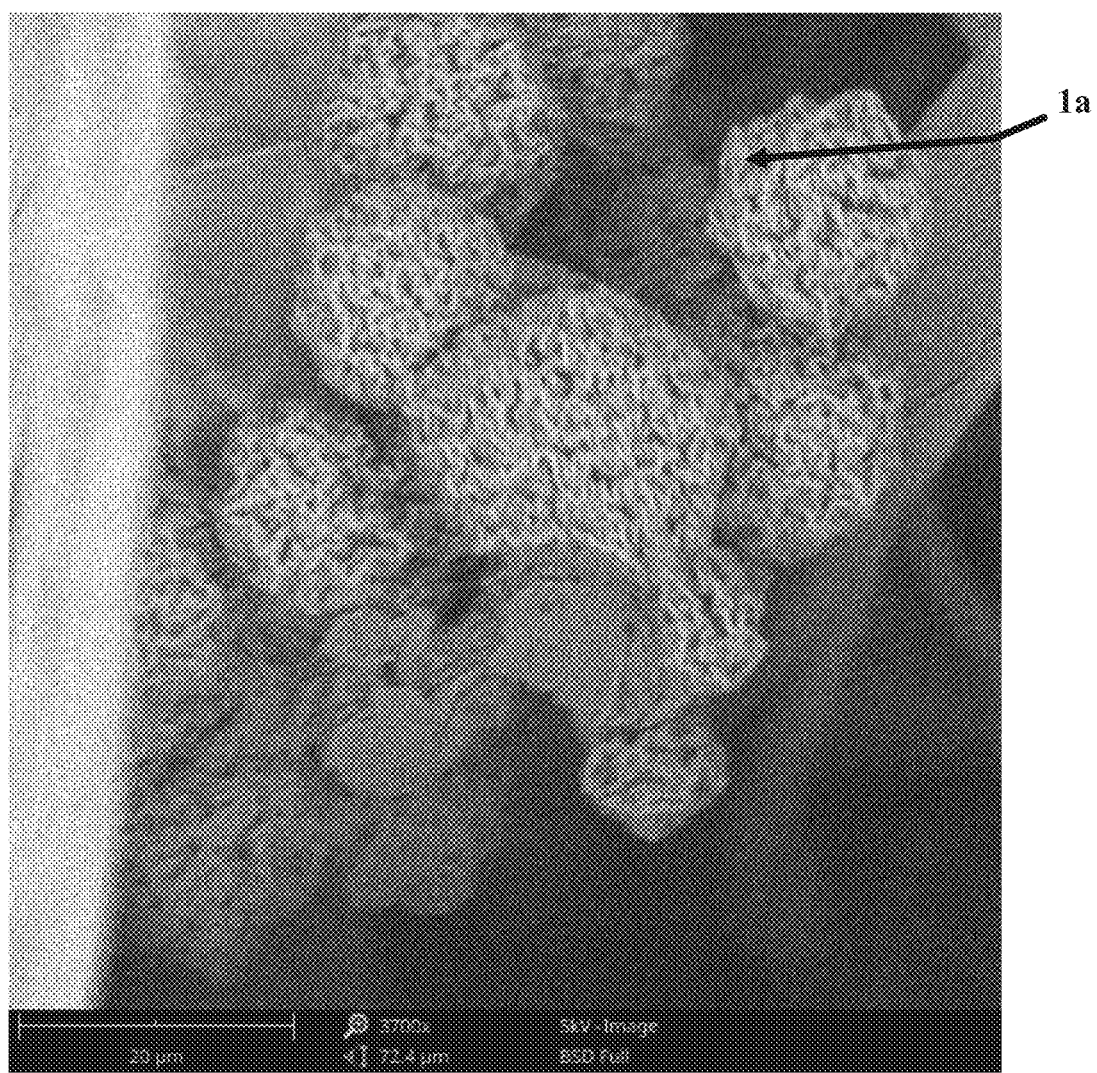
FIG. 1A shows a Scanning Electron Micrograph (SEM) of a fabric wherein COMPARATIVE EXAMPLE capsules have been tested using the Detergent Dissolution Test Method, after having been aged in liquid detergent for 1 week at 37° C. Arrow 1a shows deflated, nonintact capsules that are completely wrinkled, indicating that these capsules have lost a significant amount of encapsulated active material.
Figure 1B:
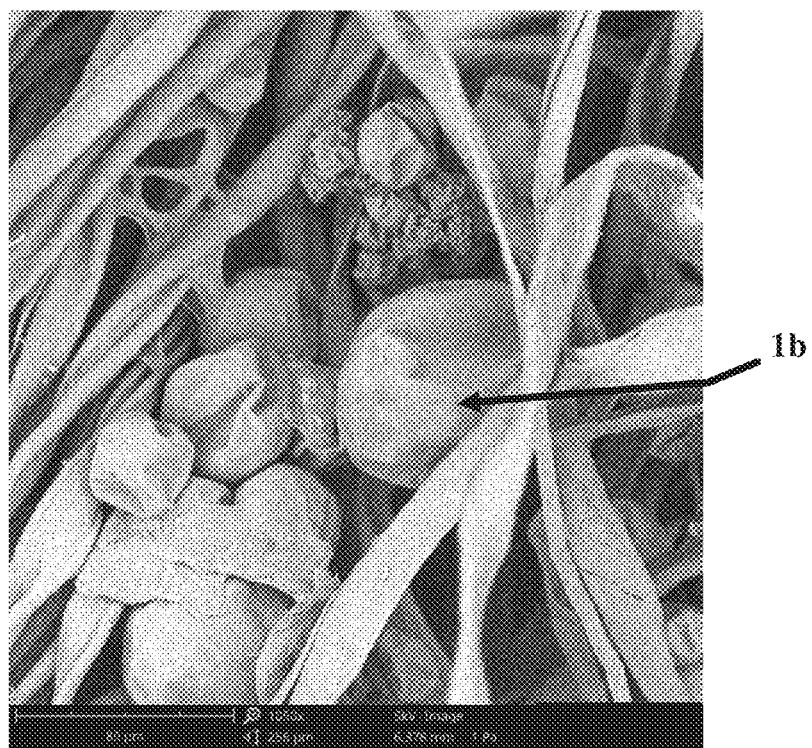
FIG. 1B shows a Scanning Electron Micrograph (SEM) of a fabric wherein Example 1 capsules have been tested using the Detergent Dissolution Test Method, after having been aged in a liquid detergent for 1 week at 37° C. Arrow 1b shows intact capsules.
Figure 2:
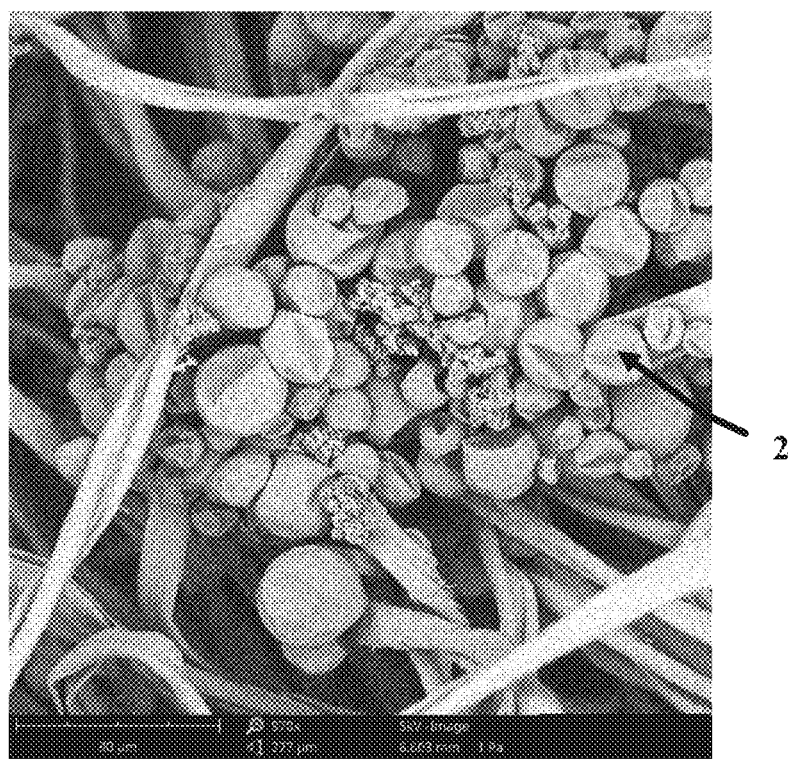
FIG. 2 shows a SEM of fabric wherein Example 2 capsules have been tested using the Detergent Dissolution Test Method, after having been aged in a liquid detergent for 1 week at 37° C. Arrow 2 shows deflated but intact capsules, clearly have a volume of internal phase, and high density of deposition on fabric.
Figure 3:
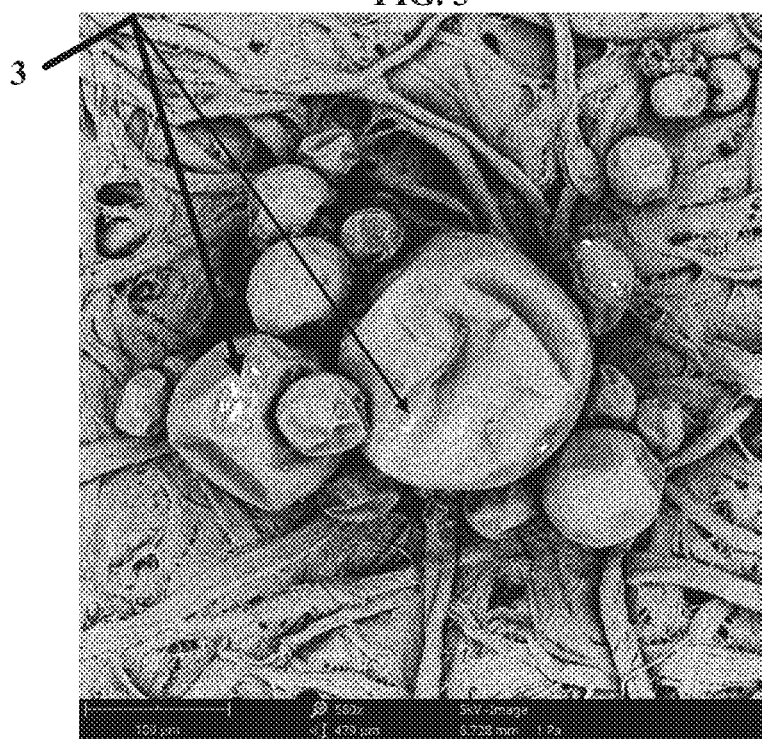
FIG. 3 shows a SEM of fabric wherein Example 3 capsules have been tested using the Detergent Dissolution Test Method, after having been aged in a liquid detergent for 1 week at 37° C. Arrow 3 shows areas of the capsule surface where talc inorganic particle has been embedded in the wall.
Figure 4:
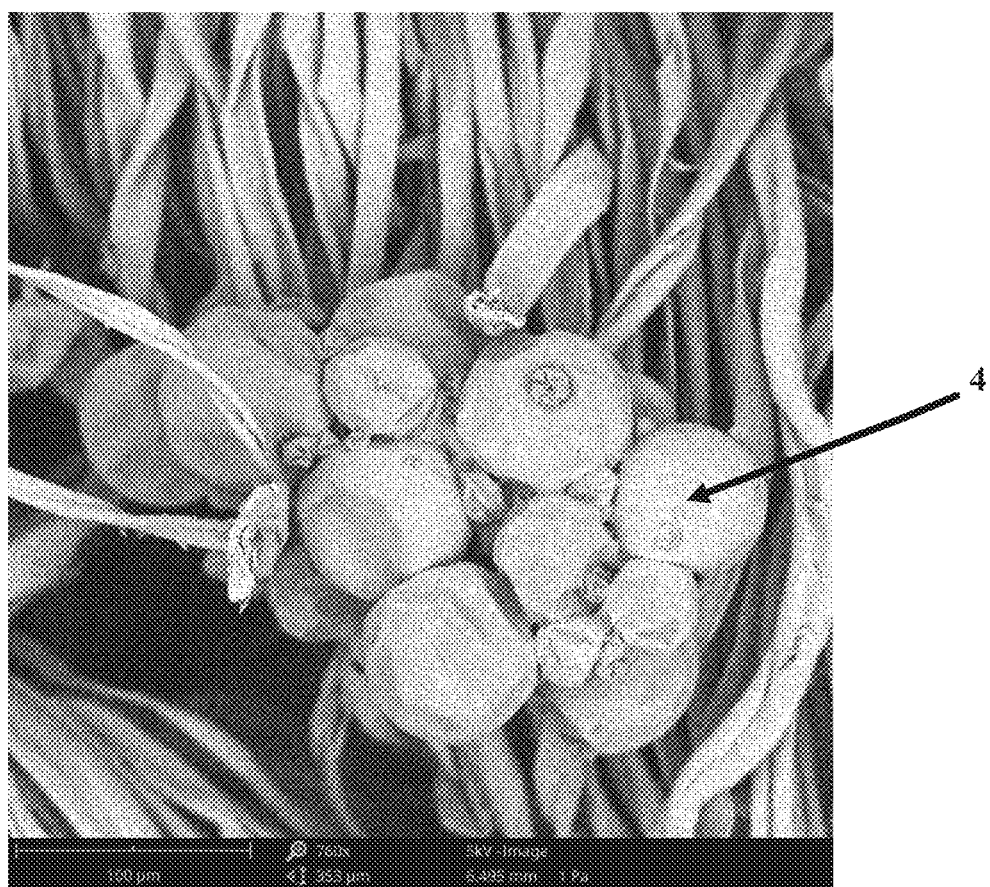
FIG. 4 shows a SEM of fabric wherein Example 4 capsules have been tested using the Detergent Dissolution Test Method, after having been aged in a liquid detergent for 1 week at 37° C. Arrow 4 shows full, intact, capsules that have a smooth surface devoid of pores, even after aging in a liquid detergent for 1 week at 37° C. In general, such capsules have not been affected adversely by solvents, surfactants, and polymers found in a liquid detergent that can extract the encapsulated core material.
Figure 5:
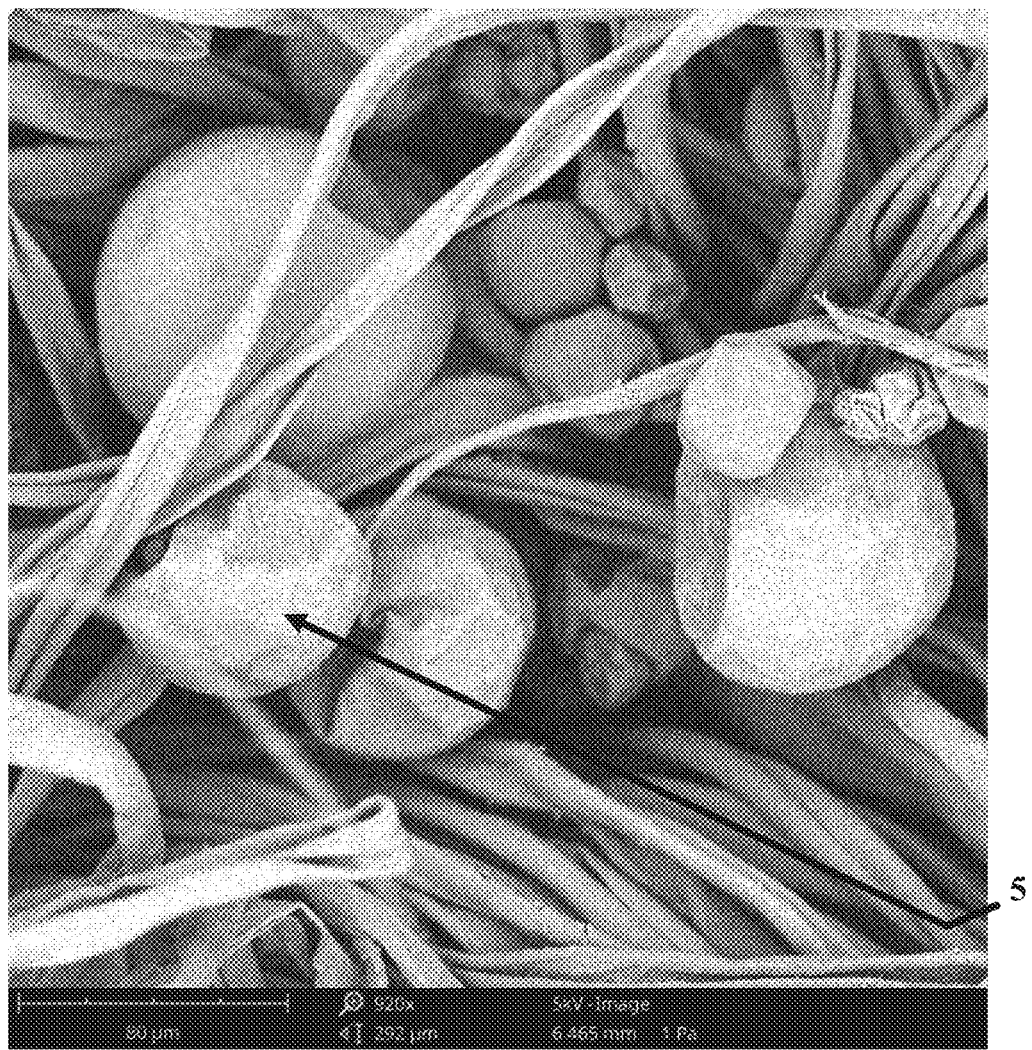
FIG. 5 shows a SEM of fabric wherein Example 5 capsules have been tested using the Detergent Dissolution Test Method, after having been aged in a liquid detergent for 1 week at 37° C. Arrow 5 shows areas of the capsule surface where tapioca starch particles are attached to the surface of the microcapsule.
Figure 6:
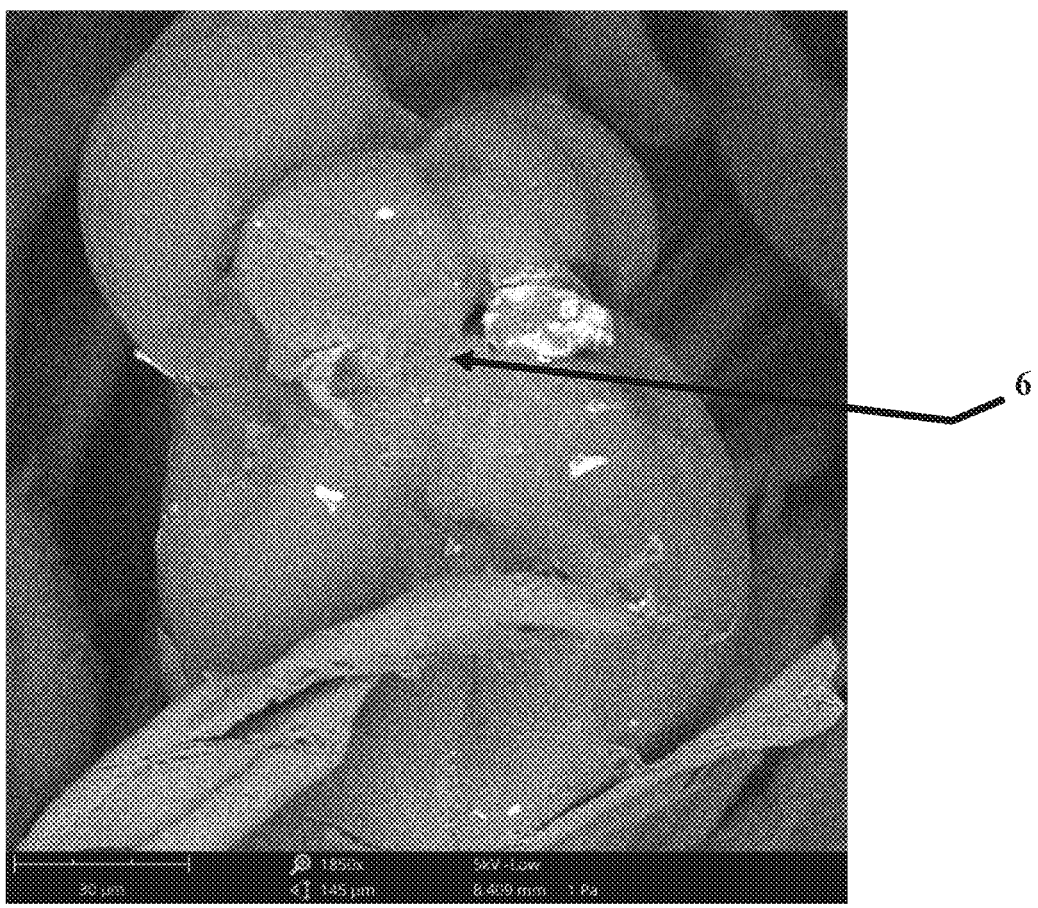
FIG. 6 shows a SEM of fabric wherein Example 6 capsules have been tested using the Detergent Dissolution Test Method, after having been aged in a liquid fabric softener for 1 week at 37° C. Arrow 6 shows a capsule that has a coating on the microcapsule and shows that the coating acts to combine two or more capsules with one another.
Figure 7:
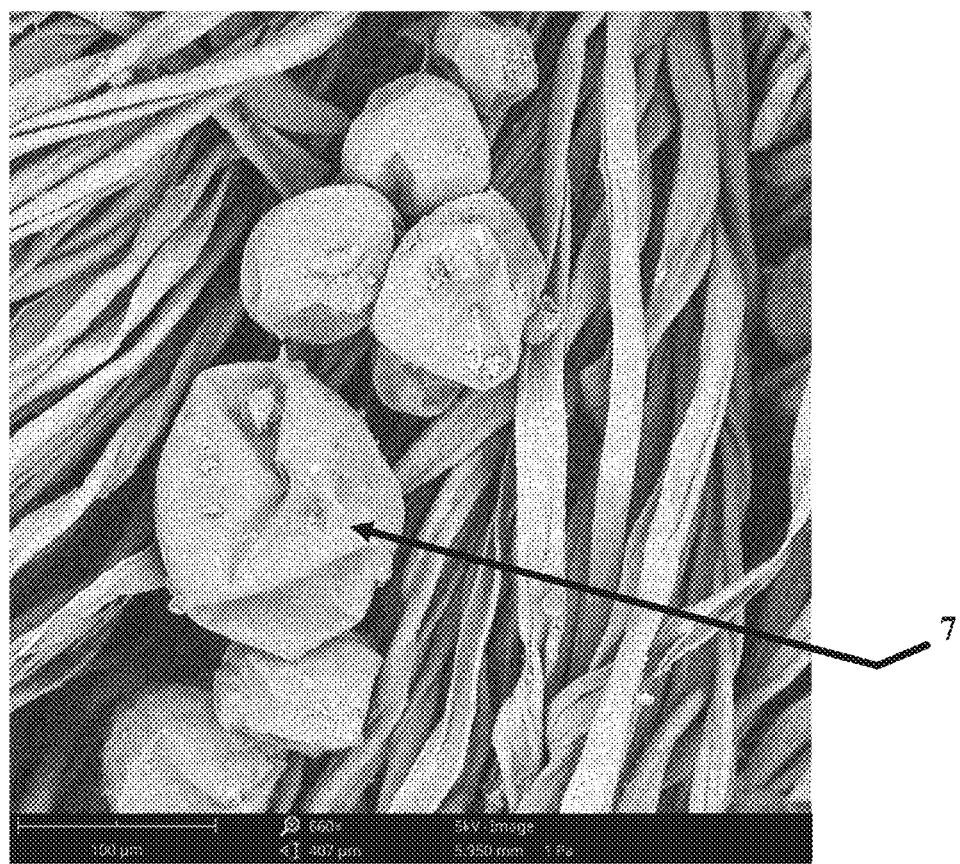
FIG. 7, FIG. 8, and FIG. 9 show SEMs of fabric wherein Example 7, Example 8, and Example 9 capsules, respectively, have been tested using the Detergent Dissolution Test Method, after having been aged in a liquid detergent for 1 week at 37° C. Arrows 7, 8, and 9 show intact capsules with a low level of deflation even after exposure of the capsules to a liquid detergent.
Figure 8:
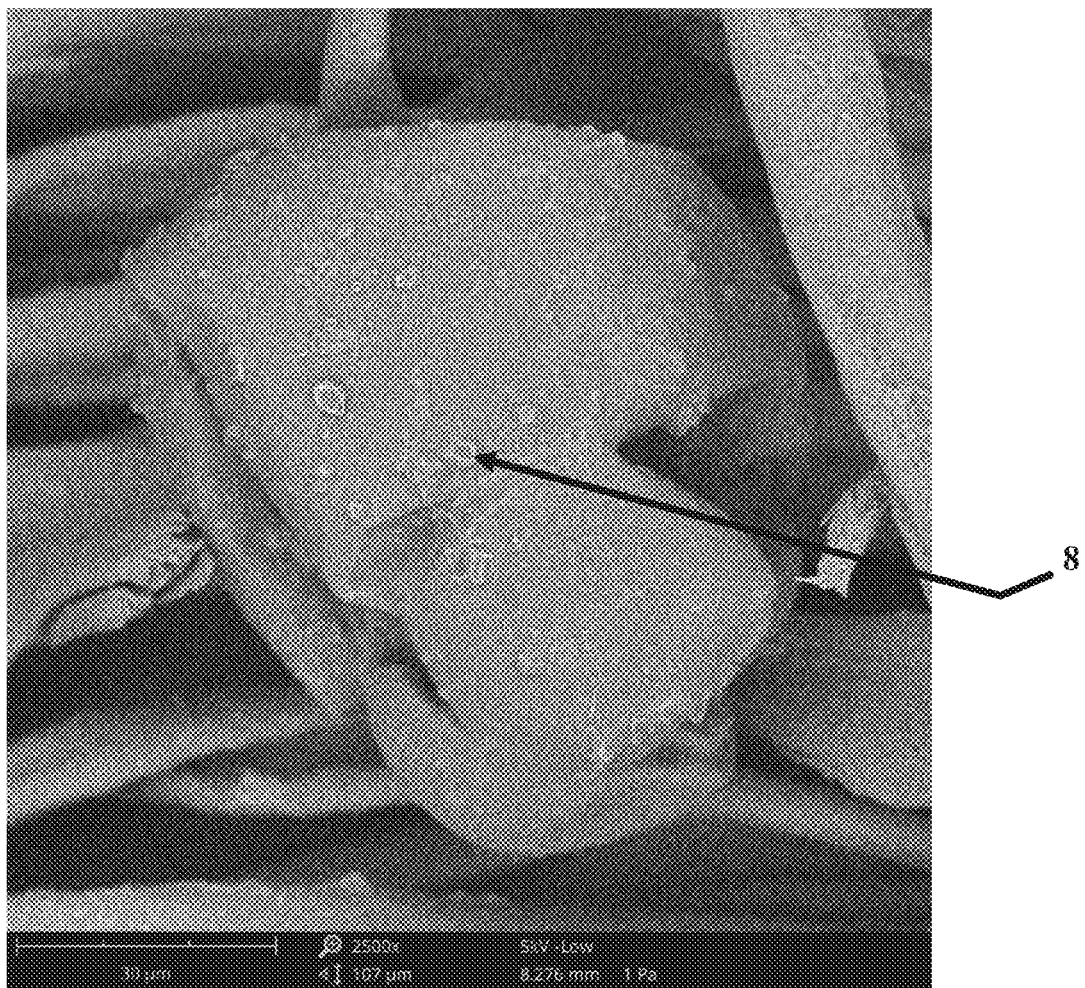
Figure 9:
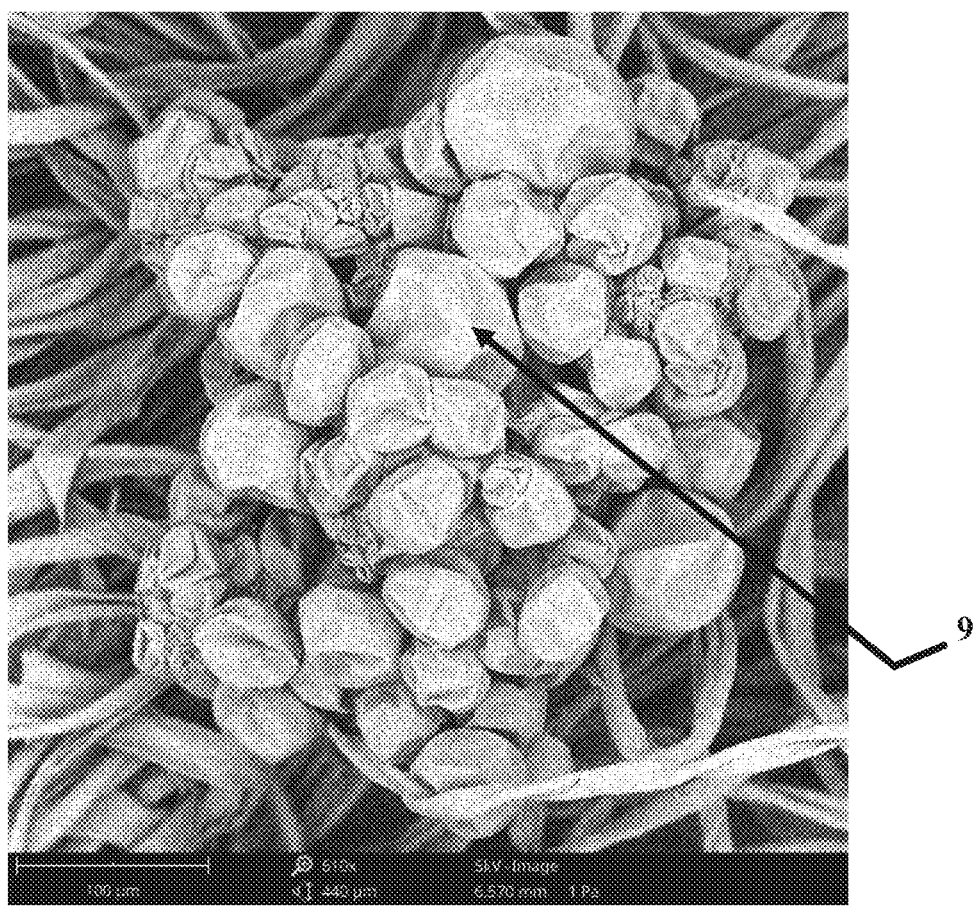
Figure 10:
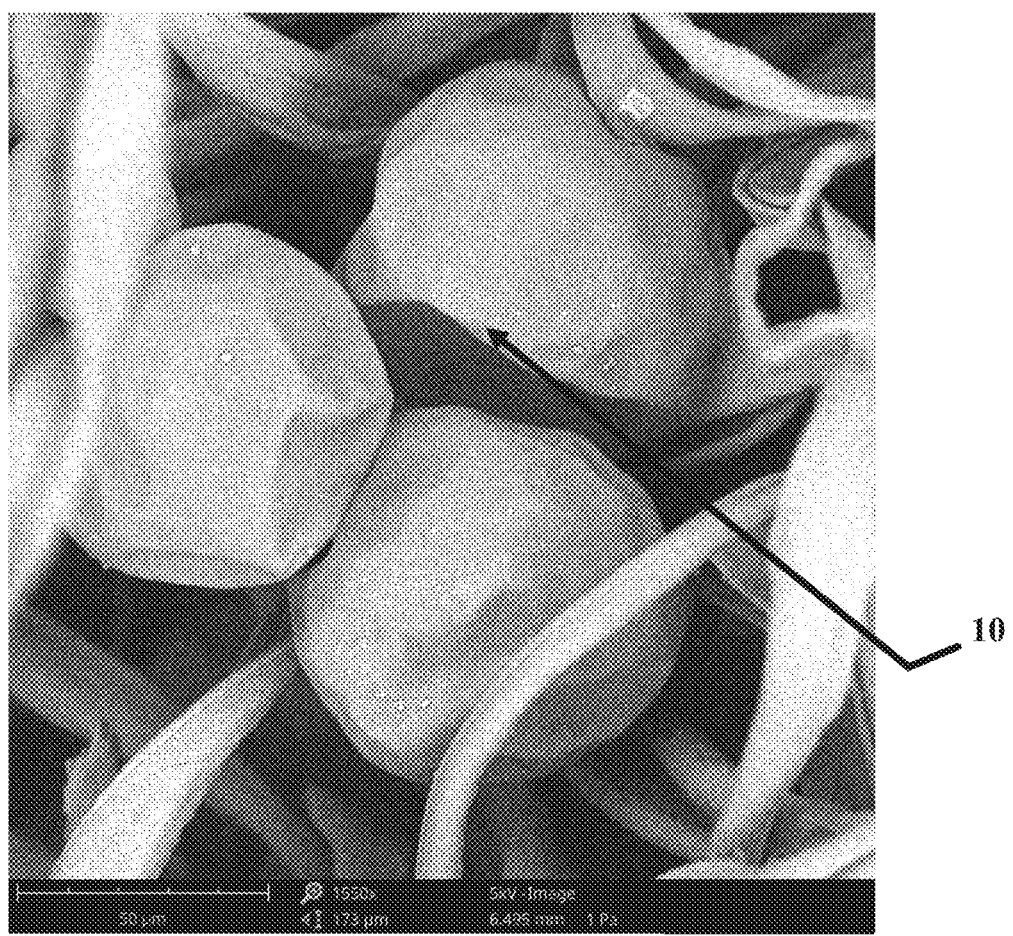
FIG. 10 shows a SEM of fabric wherein Example 4 capsules have been tested using the Detergent Dissolution Test Method, after having been aged in a liquid fabric softener for 1 week at 37° C. Arrow 10 shows full, intact, capsules that have a smooth surface devoid of pores, even after aging in a liquid fabric softener for 1 week at 37° C. In general, such capsules have not been affected adversely by solvents and low pH found in a liquid fabric softener.
Figure 11A:
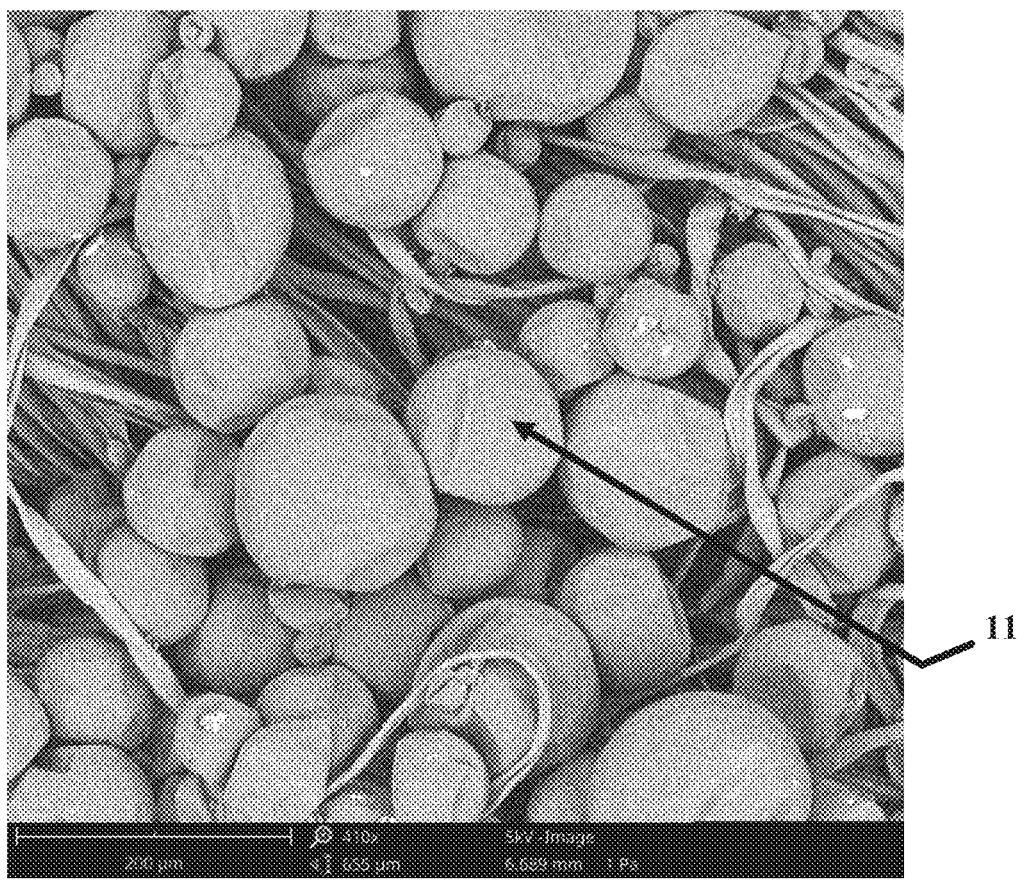
FIG. 11A shows a SEM of fabric wherein Example 6 capsules have been tested using the Detergent Dissolution Test Method, after having been aged in a liquid detergent for 1 week at 37° C. Arrow 11 shows intact, spherical capsules with low level of deflation.
Figure 11B:
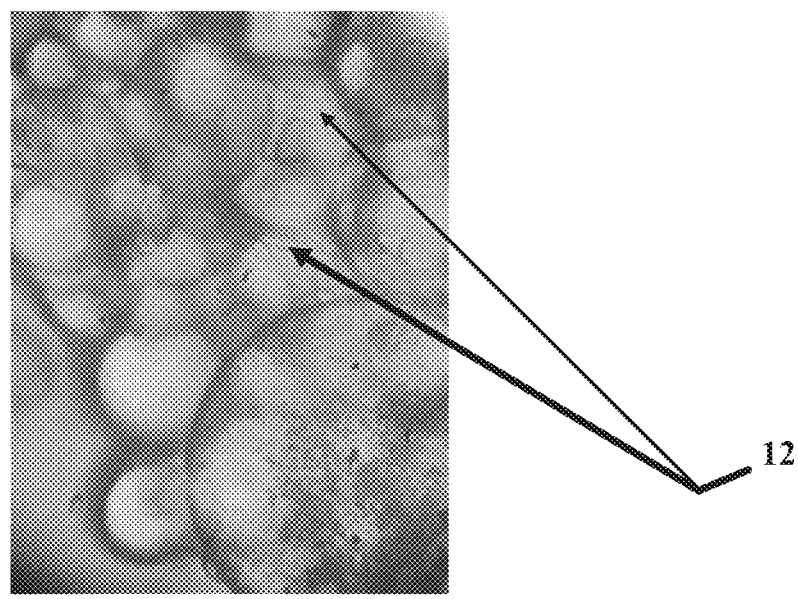
FIG. 11B shows an optical microscope of the capsules of Example 6 showing a viscoelastic polymeric coating (arrow 12) that extends from one spherical particle to another, freshly made capsules.
Figure 11C:
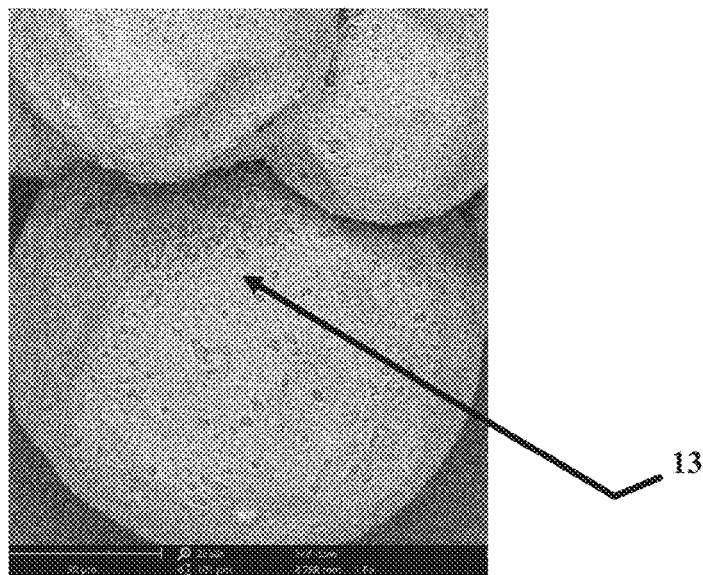
FIG. 11C shows a close-up SEM of an individual particle that has been isolated from a formulation after aging in a liquid detergent for 1 week at 37° C. Arrow 13 indicates a coating on the capsule surface.
Figure 12:
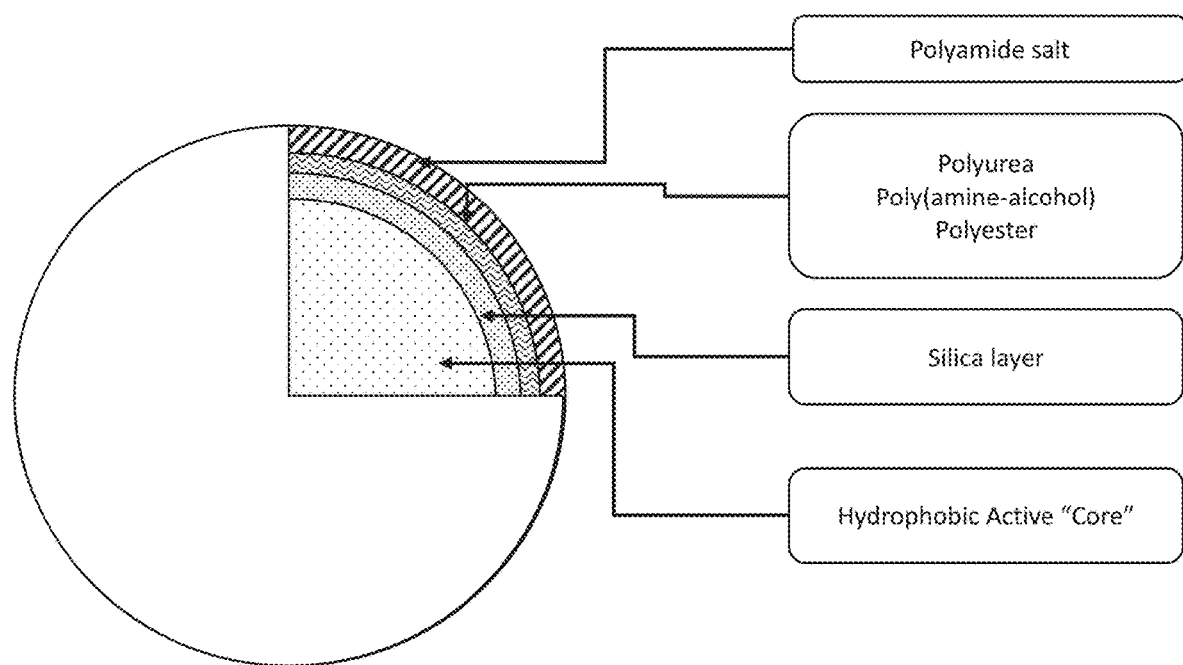
FIG. 12 shows a pictogram of Type A particles identifying the various materials that comprise the shell. Although the pictogram depicts distinct and individual layers of polymers surrounding a core, one familiar with the art will understand that this necessarily does not need to be true. The polymers can be intertwined with one another to form such a mixed membrane system.
Figure 13A:
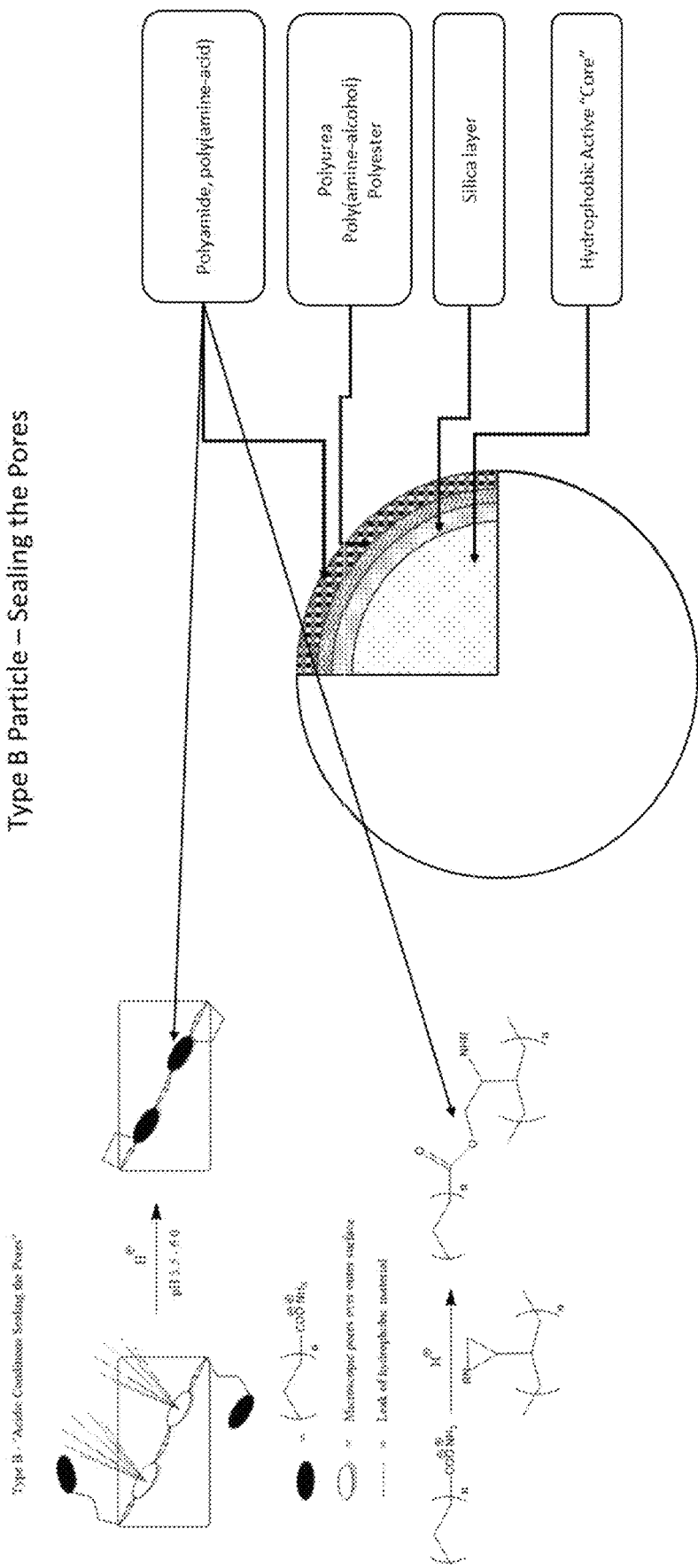
FIG. 13A shows a pictogram of Type B particles that are designed to seal the pores in the membrane that surrounds the core. Although the pictogram depicts distinct and individual layers of polymers surrounding a core, one familiar with the art will understand that this necessarily does not need to be true. The polymers can be intertwined with one another to form such a mixed membrane system. The cartoon on the left hand side shows a potential reaction chemistry that can result in sealing of the pores to minimize diffusion of the encapsulated active out of the microcapsule
Figure 13B:
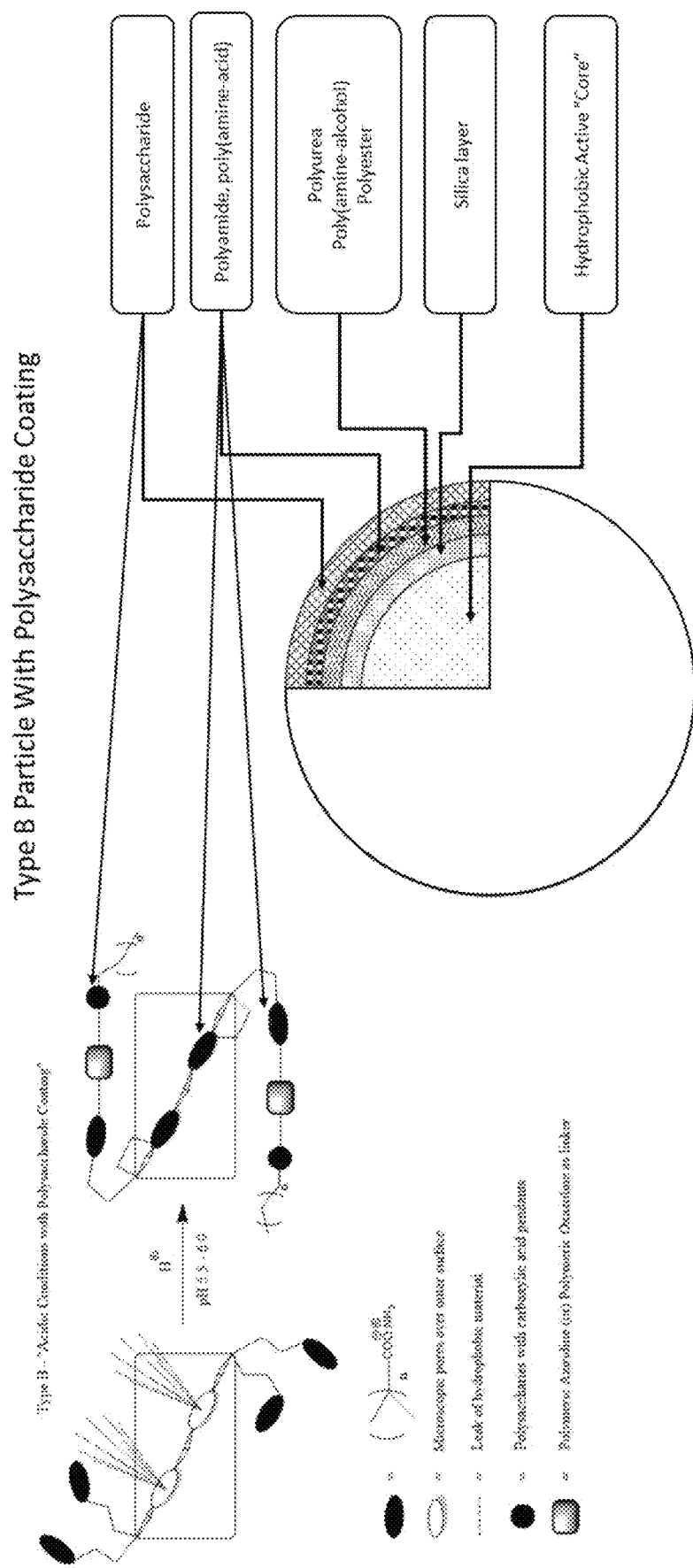
FIG. 13B shows a pictogram of Type B particles wherein sealing of the pores, as well as a polysaccharide coating is achieved under acidic conditions. Although the pictogram depicts distinct and individual layers of polymers surrounding a core, one familiar with the art will understand that this necessarily does not need to be true. The polymers can be intertwined with one another to form such a mixed membrane system. The cartoon on the left hand side shows a potential reaction chemistry that can result in sealing of the pores to minimize diffusion of the encapsulated active out of the microcapsule, as well as coating of a polysaccharide.
Figure 14:
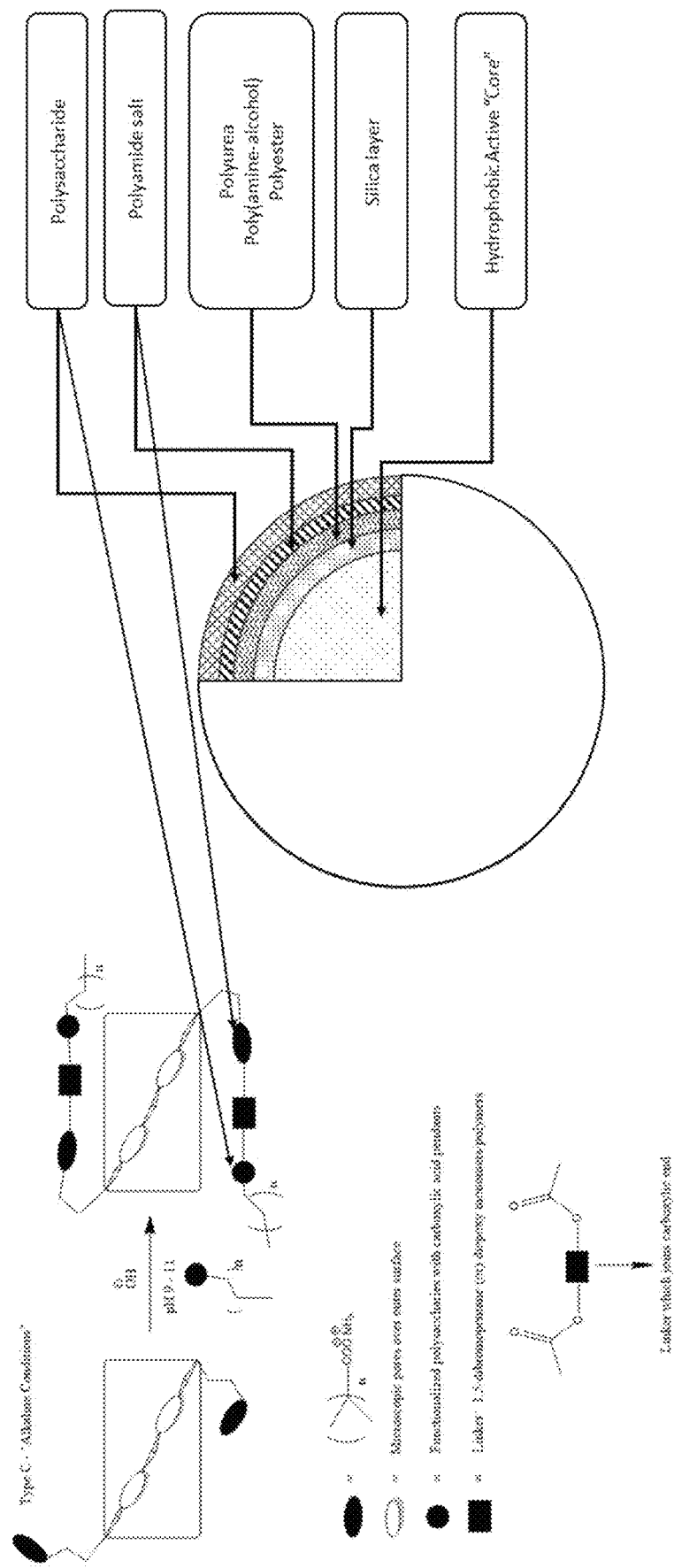
FIG. 14 shows a pictogram of Type C particles wherein a polysaccharide coating is achieved under alkaline conditions. Although the pictogram depicts distinct and individual layers of polymers surrounding a core, one familiar with the art will understand that this necessarily does not need to be true. The polymers can be intertwined with one another to form such a mixed membrane system. The cartoon on the left hand side shows a potential reaction chemistry that can result in achieving a coating of a polysaccharide.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell," "membrane" and "wall" are synonyms, which refer to barriers at least partially surrounding the core of the particles of the invention.

As used herein, microcapsules "formed under acidic conditions" means that part of the process of forming the microcapsule involves a step where the pH of the suspension in which the microcapsules form is adjusted into the acidic region (less than 7).

As used herein, microcapsules "formed under basic conditions" means that part of the process of forming the microcapsule involves a step where the pH of the suspension in which the microcapsules form is adjusted into the alkaline region (greater than 7).

As used herein, "an unreacted amount" refers to the amount of a reactant not used up in one or more reaction. "An unreacted amount" can be zero to any amount depending on the amount of reactants added.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to 2% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Advantages of the Invention

One or more of the following benefits are provided by preferred embodiments of the invention.

The inventive particles' shell material have an environmental biodegradability greater than 50% as measured by the OECD 301D method that utilizes biological oxygen demand as the criteria for measuring degradability. Conventional capsules utilize polymers that may be biodegradable prior to shell formation, but due to the nature of crosslinkers that are used and the chemical structure of the final crosslinked polymer, microbes are no longer able to attach to the polymer or the backbone to sufficiently degrade the shell material. The inventive particles utilize monomers that retain degradable functional groups even after the crosslinking is complete, such that microbes in the environment are able to digest the shell material.

The inventive particles adhere onto desired substrates via the use of viscoelastic and electrostatic interactions. By adhering large particles as well as small particles during the rinse off application, greater volumes of active material can be delivered with a higher delivery efficiency of the encapsulated active. Conventional capsules are limited to the deposition of small particles, which carry much less volume of active material. Only a fraction of these small microcapsules fracture during use, resulting in significantly lower delivery efficiency of the encapsulated active. Moreover, inventors have discovered formulation approaches to control the level of aggregation of capsules such that a higher quantity of microcapsules can be retained onto the substrate during a rinse-off or filtration process. Such discovery can reduce the quantity of capsules that are lost in the rinse water, and can reduce the environmental impact.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active. Improvement of retention of capsules onto the fabric during rinse-off processes also has the potential to reduce cost.

Particles

The invention addresses one or more of the prior art deficiencies described above by providing controlled release particles. The particles are particularly well-suited for use in encapsulation of hydrophobic, nonpolar materials.

The particles are preferably used in a consumer product composition, such as, e.g., a cleaning composition, a fabric care composition and/or a personal care composition.

The particles preferably comprise a hydrophobic active ingredient surrounded by a wall material that comprises a mixture of several different polymers—a polyurea, a poly (amine alcohol), a silica, a polyamide, a polyester, polysaccharide, and optionally, a quaternary amine.

The polyurea preferably comprises a reaction product of 1) an isocyanate functionality and 2) an amine functionality. Preferably, the isocyanate functionality is provided by polymeric isocyanates with a molecular weight greater than 300 grams per mole. Preferably, the amine functionality is provided by, for example, acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, pentaethylene hexamine, hexamethylenetetramine, tetraethylene pentamine, and quaternary amines such as Girard's reagent; silicone amines such as aminopropylsilsesquioxane oligomer, water borne amino alkyl silsequioxane oligomers, trihydroxysilylpropylamine condensate, 3-aminopropyl(diethoxy)methylsilane, [3-(2-aminoethyl)-aminopropyl] methyl-dimethoxysilane, [3-(2-aminoethyl)-aminopropyl]trimethoxysilane.

The poly(amine alcohol) preferably comprises a reaction product of 1) an epoxy and 2) an amine functionality. The silica preferably comprises the product of silica hydrolysis. The polyamide in Type B and Type C particles is preferably a reaction product of 1) a copolymer of maleic anhydride and 2) an amine functionality. The polysaccharide coating is achieved either via:

1) a reaction of the alcohol groups with the isocyanate (Type A or Type B particles) or 2) the reaction of free acid of the copolymer of maleic anhydride and free acid of carboxy modified polysaccharide reacted with either polyaziridine or polyoxazoline under acidic conditions or 3) the reaction of carboxylate functional groups on a modified polysaccharide with the carboxylate groups of the copolymer of maleic anhydride via a polyfunctional linker (Type C particles) under alkaline conditions.

The quaternary amine is preferably a material that has a primary amine moiety and a quaternary amine moiety. The primary amine moiety can preferably react with isocyanate functionality to form a polyurea layer, and the highly polar quaternary amine functionality interacts with the surrounding aqueous phase. Suitable quaternary amine materials include, for example, Girard's reagent. Other suitable quaternary amines include but are not limited to compounds represented by formulas (1)-(4) below.

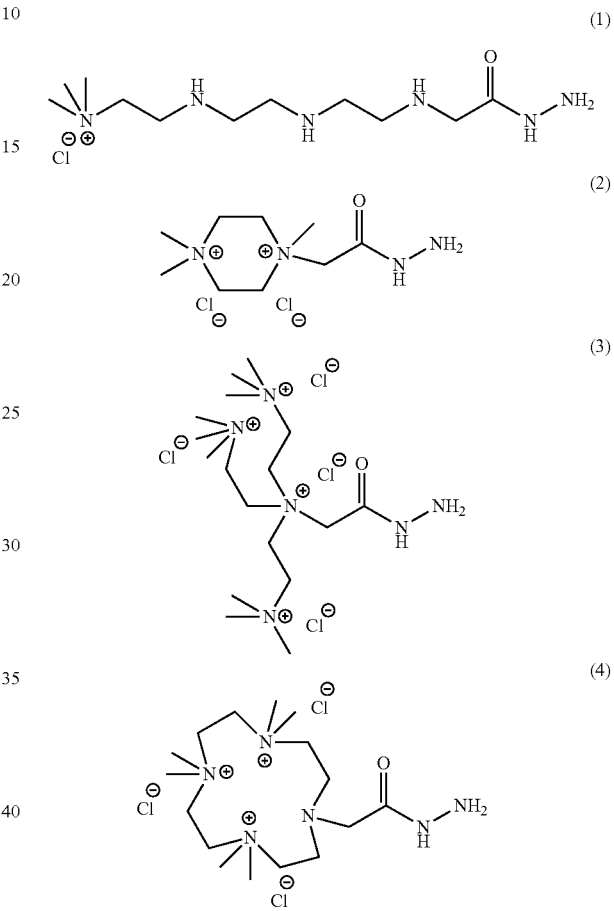

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 47 wt. % or 59 wt. % or 66 wt. % to 73 wt. % or 78 wt. % or 81 wt. % or 93.5 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a pheromone, phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, neobee, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Suitable moldicides further include but are not limited to fungicidal compounds such as, e.g., isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethyl-isothiazolinone, 4,5-Dichloro-2-n-octyl-3 (2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point.

Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying agents include unsaturated natural resins such as rosin or derivatives thereof, such as rosin esters of polyols such as glycerol or pentaerythritol, hydrogenated rosins or dehydrogenated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

The emulsifier is present in the suspension, on a dry basis (weight of emulsifier per weight of dry matter in the suspension), of the invention in an amount effective to achieve the desired particle size distribution. The amount can be, e.g., from about 1.5 wt. % to about 10 wt. % or at least 1.5 wt. %, or at least 5 wt. % or at least 7.4 wt. % or at least 8.2 wt. %, or at least 10 wt. % or not greater than 20 wt. %.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17. Of course, emulsifiers/surfactants of lower and higher HLB values that achieve the same objective as noted are also included.

Exemplary emulsifiers include, but are not limited to gums such as acacia gum, gum arabic, konjac gum, and xantham gum; poly(meth)acrylic acids and derivatives. Most preferably, the emulsifier/emulsion stabilizer is a polyvinyl pyrrolidone, copolymers of polyvinyl pyrrolidone with vinyl acetate, vinyl alcohol, vinyl imidazole; polyglycerol oleates.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelalkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesuifonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy-modified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, 1H-Imidazolium, 1-ethenyl-3-methyl-, chloride, polymer with 1-ethenyl-2-pyrrolidinone, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; sorbitol ester alkoxylates; ethoxylated castor oil; amides of fatty acids such as stearamide, lauramide diethanolamide, and lauramide monoethanolamide; aryl ethers of polyoxyalkylene glycols such as polyoxyethylene glycol nonylphenyl ether and polypropylene glycol stearyl ether. Also preferred as non-ionic emulsifiers are various latex materials, stearates, lecithins, The amine comprises linear aliphatic amines, aromatic amines, silicone amines, branched amines, polyamines, and amino acids. Generally, amines are listed by their pKa values, and this defines whether the amine is acidic, basic, or neutral. Acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, guanidine carbonate. pentaethylene hexamine, hexamethylenetetramine, tetraethylene pentamine, and Girard's reagent; silicone amines such as aminopropylsilsequioxane oligomer, water borne amino alkyl silsequioxane oligomers, trihydroxysilylpropylamine condensate, 3-aminopropyl(diethoxy)methyl-silane, [3-(2-aminoethyl)-aminopropyl]methyldimethoxysilae, [3-(2-aminoethyl)-aminopropyl]tri-methoxysilane; guanidine carbonate; amino acids such as Aspartic acid, glutamic acid, lysine, arginine, histidine, glycine, alanine, serine, threonine, tyrosine, asparagine, glutamione, cysteine.

The amine is present in particles of the invention in an amount effective to react with the isocyanate moiety, the organofunctional silane moiety, the epoxy moieties to an extent effective to provide the particles with desired durability. The amount of amine on a dry basis (weight of amine per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates. Exemplary isocyanates are selected from the group consisting of hexamethylene diisocyanates (Desmodur N3600, Desmodur N3800, Desmodur N3900, Desmodur N3200, Desmodur N3300, Desmodur N3400, Takenate D-170N), isophorone diisocyanates (Desmodur XP2565, Desmodur Z4470), blends of hexamethylene diisocyanate and isophorone diisocyanate (Desmodur XP2847, Desmodur XP2489, Desmodur XP2838, Desmodur XP2763), pentane-1,5-diisocyanate (Stabio D-370N, Stabio D-376N), xylylene diisocyanate (Takenate 500, Takenate 600, Takenate D-110N, Takenate D-131N), polymeric methylene diphenyl diisocyanate (Mondur MR Lite), polymeric MDI (Desmodur VK 5, Desmodur VL R10, Desmodur 44V40L, Desmodur 44V70L), polyether modified hydrophilic polyisocyanates (Bayhydur XP2451/1, Bayhydur XP2547, Bayhydur XP2759, Bayhydur Ultra 304, Bayhydur Ultra 2487/1), CN9302, ionically modified isocyanates (Bayhydur 2858 XP, Bayhydur XP2759, Bayhydur eco 7190), and the like.

In certain embodiments, the organofunctional silane as at least one member selected from the group consisting of alkoxylated silane, trialkoxy silanes, functionalized trialkoxysilanes (amino, glycidoxy, methacryloxy, vinyl), tetraalkoxylated silanes including tetramethoxy silane and tetraethoxy silane, 1,2-bis(triethyxysilyl)ethane.

The organofunctional silane is present in particles of the invention in an amount effective to hydrolyze in water and react with the amine moiety to create Si—O—Si bonds. The amount of amine on a dry basis (weight of organofunctional silane per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the epoxide curing agent is at least one member selected from the group consisting of low temperature curing agents having 2 or more epoxy functional groups which are terminally located. Suitable materials include trimethylol propane triglycidyl ether, resins containing acrylate and epoxy functional groups, diepoxide of the cycloapliphatic alcohol, hydrogenated Bisphenol A, resorcinol/bisphenol F resin with polyfunctional epoxide resin blend.

The epoxide curing agent is present in particles of the invention in an amount effective to react with amine moiety, isocyanate moiety, and/or the hydrolyzed organofunctional silane moiety. The amount of epoxide curing agent on a dry basis (weight of epoxide curing agent per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the copolymer of maleic anhydride is at least one member selected from the group consisting of unsaturated acidic reagents which readily react with nucleophiles such as alcohols and amines to form corresponding esters and amides. Preferably, such reagents hydrolyze in presence moisture to deliver a free acid. Suitable materials include the free radical polymerization reaction products of maleic anhydride with acyclic or cyclic or vinylic aromatic alkenes to form co-polymers with varying molecular weights and degree of maleic anhydride levels. Suitable materials include poly(ethylene-alt-maleic anhydride), poly(methyl vinyl ether-alt-maleic acid), poly(methyl vinyl ether-alt-maleic acid monoethyl ester), poly(isobutylene-alt-maleic anhydride) amide ammonium salts, poly(styrene-alt-maleic acid) sodium salt, poly(4-styrene-sulfonic acid-co-maleic acid) sodium salt, poly(isobutylene-alt-maleic anhydride), and the like.

The copolymer of maleic anhydride is present in particles of the invention in an amount effective to react with amine moiety to a carboxylate anion. Acidification of the anion results in the generation of an acid. Subsequently, the acid can react with the isocyanate moiety, and/or aziridine moiety. The amount of copolymer of maleic anhydride on a dry basis (weight of copolymer of maleic anhydride per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the polyaziridine comprises a member selected from the group consisting of polymers having at least 2 aziridine functional groups as terminal or pendant groups.

The polyaziridine is present in particles of the invention in an amount effective to react with carboxylic acid moieties. The amount of polyaziridine on a dry basis (weight of polyaziridine per weight of dry matter in the suspension) can be, e.g., from 0.1 wt. % or 0.4 wt. % or 0.6 wt. % or 1.0 wt. % to 1.4 wt. % or 2.0 wt. % or 3.8 wt. %.

In certain embodiments, the inorganic solid particles comprise a member selected from the group consisting of organically modified or water insoluble clays, minerals, salts such as talc, calcium carbonate, bentonite.

The inorganic solid particles are present in particles of the invention in an amount effective to improve the barrier properties of the membrane. The amount of inorganic solid particles on a dry basis (weight of inorganic solid particles per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the polysaccharide comprise a member selected from the group consisting of natural starches such as tapioca, potato, corn, rice, wheat; modified starches such as carboxy modified polysaccharide or cellulose such as carboxymethyl starch, carboxymethyl chitosan, chitosan oligosaccharide, hydroxy propyl methyl starch, hydroxy propyl cellulose, ethyl cellulose, methyl cellulose, and octenyl succinic anhydride modified starch.

The polysaccharides are present in particles of the invention in an amount effective to improve the environmental biodegradability of the particles. The amount of polysaccharides on a dry basis (weight of polysaccharide per weight of dry matter in the suspension) can be, e.g., from 0.1 wt. % or 0.4 wt. % or 0.6 wt. % or 1.0 wt. % to 1.4 wt. % or 2.0 wt. % or 3.8 wt. %.

In certain embodiments, the polyoxazolines comprise a member selected from the group consisting of A polymer with more than two oxazoline functionality as a terminal group or pendant group of a polymeric backbone. The polyoxazolines are present in particles of the invention in an amount effective to improve the barrier properties of the membrane. The amount of polyoxazolines on a dry basis (weight of polyoxazolines per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the carbodiimide comprises a member selected from the group consisting of waterborne polycarbodiimide resin, copolymer containing carbodiimide and isocyanate functionalities, copolymer containing carbodiimide and epoxy functionalities, ethyl carbodiimide hydrochloride. The carbodiimide is present in particles of the invention in an amount effective to improve the barrier properties and environmental biodegradability of the membrane. The amount of carbodiimide on a dry basis (weight of carbodiimide per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the polyfunctional linkers comprise a member selected from the group consisting of polymers having at least two functional groups that are capable of reacting with carboxylate groups as a terminal group or pendant group. Suitable materials include aliphatic dihaloalkanes such as 1,3-dibromopropane, 1,4-dibromobutane, 1,5-dibromopentane, 1,6-dibromhexane, 1,7-dibromoheptane, and cyclic comprising dibromo isomers of cyclobutene, cyclopentane, cyclohexane, cyclooctane; diepoxides such as 1,4-butanediol diglycidyl ether and diepoxybutane, diepoxides of both unsaturated and hydrogenated bisphenol A; polyfunctional epoxides such as castor oil glycidyl ether, epoxidized soybean oil, and the like.

The polyfunctional linkers are present in particles of the invention in an amount effective to react carboxylate functional groups that improve the barrier properties and environmental biodegradability of the membrane. The amount of polyfunctional linkers on a dry basis (weight of polyfunctional linkers per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %_____.

In certain embodiments the epoxy is at least one member selected from the group consisting of epoxidized unsaturated oils such as epoxidized soybean oil, epoxidized vegetable oil, and the like; epoxidized alcohols such as isoborbide glycidyl ether, polyglycerol-3-glycidyl ether, castor oil glycidyl ether; epoxidized polysaccharides such as sorbitol polyglycidyl ether, EX-201: Resorcinol Diglycidyl Ether; EX-211: Neopentyl Glycol Diglycidyl Ether; EX-212: 1,6-Hexanediol Diglycidyl Ether; EX-252: Hydrogenated Bisphenol A Diglycidyl Ether; EX-313: Glycerol Polyglycidyl Ether; EX-314: Glycerol Polyglycidyl Ether; EX-321: Trimethylolpropane Polyglycidyl Ether; EX-411: Pentaerythritol Polyglycidyl Ether; EX-421: Diglycerol Polyglycidyl Ether; EX-512: Polyglycerol Polyglycidyl Ether; EX-612: Sorbitol Polyglycidyl Ether; EX-711: Diglycidyl Terephthalate; EX-721: Diglycidyl o-Phthalate; EX-731: N-Glycidyl Phthalimide; EX-810: Ethylene Glycol Diglycidyl Ether; EX-811: Ethylene Glycol Diglycidyl Ether; EX-850: Diethylene Glycol Diglycidyl Ether; EX-851: Diethylene Glycol Diglycidyl Ether; EX-821: Polyethylene Glycol Diglycidyl Ether; EX-920: Polypropylene Glycol Diglycidyl Ether; EM-160: Emulsion of Epoxy Cresol Novolac Resin; DENACOL FCA-640: Hexahydrophthalic acid diglycidyl ester; and the like, available from Nagase.

The epoxy is present in particles of the invention in an amount effective to react with the amine moiety, the isocyanate moiety, and/or the hydrolyzed organofunctional silane moieties. The amount of epoxy on a dry basis (weight of epoxy per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof; polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, 1H-Imidazolium, 1-ethenyl-3-methyl-, chloride, polymer with 1-ethenyl-2-pyrrolidinone, polyamines, polysaccharides with cationic modification, and mixtures thereof. Polysaccharides can be employed with cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The deposition aid is present in the controlled release particles in an amount on a dry basis (weight of deposition aid per weight of dry matter in the suspension) from 0.5 wt. % or 1 wt. % or 1.5 wt. % or 3.5 wt. % to 5 wt. % or 7 wt. % of the weight of the particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles according to the present teaching are made in a multi-step process as described below. For convenience, the process is presented in the preferred mode which involves one aqueous phase composition and one hydrophobic oil phase composition. Nonetheless, those skilled in the art will readily appreciate that the aqueous phase composition may be prepared as a dual phase composition to which the hydrophobic oil phase composition is added or a three or more components composition where various ingredients are preferably isolated from one another until desired so as to avoid undue or undesired activation of the aqueous phase monomers or oligomers.

The hydrophobic oil phase composition is formed by combining the hydrophobic active core material with oil soluble monomers and oligomers. Most preferably this is conducted under moderate increased temperature so as to facilitate the solubilization or suspension of the monomers, oligomers, and other ingredients that may be present, including nucleating agents, in the core material. This is particularly useful if the core material is a solid or wax or a high viscosity material. Once again, if the temperature of the mixture had been elevated to aid in getting the hydrophobic oil phase monomer into solution/suspension, then the mixture should be cooled or allowed to cool to ambient temperature.

Materials that are not necessarily soluble or miscible in the oil phase can also be dispersed in the oil phase. The purpose is to maintain these materials at the oil-water interface to improve the properties of the membrane. In the present invention, polysaccharides, inorganic solid particles, and plasticizers are often materials that are not miscible in oil; however, they influence the barrier properties, flexibility, and biodegradability properties of the membrane.

The hydrophobic oil phase composition is added to an aqueous phase to form an emulsion. The mixture is agitated until the desired droplet size of oil phase composition is attained. In order to establish a wall at the oil-water interface, an amine is added to the aqueous phase followed by pH adjustment. Droplets are preferably from about 10 microns to about 75 microns, and more preferably from about 20 microns to about 50 microns in volume average diameter.

Not to be limited by theory, the amine added in the aqueous phase can react with several functional groups present in the hydrophobic oil phase, including isocyanate, epoxy, and organofunctional silane. The reactivity of amine is higher with isocyanate, and therefore provides the outer membrane via an interfacial polymerization reaction that limits the diffusion of the hydrophobic oil phase into the surrounding aqueous phase. Not to be limited by theory, the amine next reacts with epoxy functionality to form amino alcohols. The amino alcohols can in turn react with the isocyanates, such reaction will lead to the possible formation of polyurethanes and polyureas which will reduce the permeability of the membrane. Introduction of the hydrophobic oil phase into the aqueous phase can hydrolyze the organofunctional silanes. Such silanes self-condense in the presence of amine to form a cage structure comprising Si—O—Si bonds to reduce permeability of the membrane. In Type B particles, once the amine has reacted and is present on the surface of the particle, it can react with the copolymer of maleic anhydride to open up the anhydride ring to produce amide and carboxylate anion. Upon acidification of such anions, using aqueous inorganic or organic acids, will generate a free carboxylic acid. Such acid can then react with any residual isocyanate functional groups, or it can react with polyaziridines that are pre-dissolved in the oil phase and leaking out through the micropores in the membrane of the microcapsules to further reduce the permeability of the membrane by "sealing the pores". The presence of carboxy modified polysaccharides in the aqueous phase can also result in reaction with polyaziridines, further reducing the permeability of the membrane and improving the environmental biodegradability. In cases where it is not desired to acidify, due to the stability of the hydrophobic oil phase to changes in pH, Type C particles can be pursued. The addition of polyhaloalkanes or polyepoxy motifs in an alkaline environment can facilitate the reaction of carboxylate functional groups on the capsule surface (from the maleic anhydride ring opening) with carboxyl functional groups on the polysaccharides or celluloses added to the water phase.

Inventors have discovered that pursuing a high degree of crosslinking in making polyurea, polyurethane, polyester, polyamide, poly(amine-alcohol), and the like, via chemical reaction processes that comprise interfacial polymerization, polycondensation reactions, addition reactions, free radial polymerization reactions, and the like, may provide a membrane with good barrier properties and mechanical properties; however, such membranes have poor environmental biodegradability. Not to be limited by theory, a high degree of crosslinking results in the absence of both functional groups and flexibility that hinders the ability of microbes to form a biofilm around the polymer membrane followed by digestion of membrane to improve biodegradability.

Once this membrane is established, no further decrease in particle size of the oil droplets is observed. The reactor contents are agitated for 30 minutes to 5 hours, depending on the emulsifying properties of the hydrophobic oil phase. It is desired to maintain a temperature of the reactor below 40° C., in order to facilitate controlled membrane formation. It is desired to increase the temperature of the reactor contents to 60° C. for an additional 2 to 5 hours to complete the reaction.

In certain embodiments, the suspension of controlled release particles is dehydrated in order to expose the particles to a higher temperature to achieve a higher degree of crosslinking of the monomers.

In certain embodiments of providing a powder composition of the invention, spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

In powder composition embodiments, the silica flow aid is added to the dry powder to improve the flowability of the powder. Addition of the silica flow aid minimizes the agglomeration of particles during the heating, packing, and conveyance processes.

Advantages of at least some embodiments of the inventive method include at least one or at least two or at least three or at least four or at least five or at least six or at least seven or all eight of the following:
  a) One-pot process: membrane developed from oil and aqueous phases in a single process;
  b) Flexibility in active: membrane is developed at the oil-water interface via the use of interfacial polymerization;
  c) Controlled permeability of the shell;
  d) Controlled aggregation of the particles;
  e) Functionalized surface to increase the adhesion or filtration efficiency of particles onto the substrate during a rinse-off process;
  f) Favorable environmental biodegradability profile;
  g) Can be used in a variety of applications, including but not limited to household care, personal care, beauty care, etc.; and/or
  h) Preferably utilizes a commercially available, relatively inexpensive technique to further engineer the particle.

Compositions Containing the Particles

The invention further comprises compositions (e.g., products, articles of manufacture, etc.) comprising the controlled release particles. Such compositions include but are not limited baby care, beauty care, fabric & home care, family care, feminine care, health care, snack and/or beverage products or devices intended to be used or consumed in the form as sold, and not intended for subsequent commercial manufacture or modification. Such products include but are not limited to fine fragrances (e.g., perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 sec$^{-1}$ shear rate and at 21° C., of from 1 to 7000 cps and a low shear viscosity, at 0.5 sec$^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry comprising particles of the invention. Said slurry may be combined with an adjunct ingredient to form a composition, for example, a consumer product. In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose and cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol, non-polar solvents including but not limited to mineral oil, perfume raw materials, silicone oils, hydrocarbon paraffin oils, and mixtures thereof.

In certain embodiments, a perfume oil is combined with the slurry comprising microcapsules to provide multiple benefits. The emulsified perfume oil will increase the viscosity of the slurry and prevent the phase separation of the microcapsule particles. The mixture provides a way to deliver non-encapsulated and encapsulated fragrance from the same slurry.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition used for capsule making.

TABLE 1

Perfume oil composition

| Material | wt % | Functionality |
| --- | --- | --- |
| CITRONELLYL NITRILE | 1.00% | NITRILE |
| TRIPLAL | 0.25% | ALDEHYDE |
| FLORHYDRAL | 0.10% | ALDEHYDE |
| ALDEHYDE C-10 | 0.10% | ALDEHYDE |
| ALDEHYDE C-12 LAURIC | 0.20% | ALDEHYDE |
| ALLYL CYCLOHEXYL PROPIONATE | 1.00% | ESTER |
| CETALOX | 0.20% | FURAN |
| ANISIC ALDEHYDE | 0.10% | ALDEHYDE |
| CYCLACET | 10.00% | ESTER |
| CYCLAPROP | 5.00% | ESTER |
| DIHYDROMYRCENOL | 10.00% | ALCOHOL |
| DIPHENYL OXIDE | 1.00% | OXIDE |
| HABANOLIDE | 2.50% | KETONE |
| YARA YARA | 2.00% | ETHER |
| CIS-3-HEXENYL SALICYLATE | 2.00% | ESTER |
| VERDOX | 2.50% | ESTER |
| HEXYLCINNAMIC ALDEHYDE | 20.00% | ALDEHYDE |
| BHT | 0.50% | 0.0025 |
| ISO E SUPER | 2.50% | KETONE |
| KOAVONE | 2.50% | 0.0625 |
| EUCALYPTOL | 0.20% | ALCOHOL |
| MANZANATE, 10% IPM | 0.50% | ESTER |
| MUSCENONE, 10% IPM | 0.50% | KETONE |
| LAEVO CARVONE, 10% IPM | 0.50% | 0.0025 |
| METHYL ANTHRANILATE | 0.10% | ESTER |
| METHYL IONONE GAMMA | 1.25% | KETONE |
| LILIAL | 10.00% | ALDEHYDE |
| ALDEHYDE C-12 MNA, 10% DPG | 0.50% | ALDEHYDE |
| MYRAC ALDEHYDE | 0.50% | ALDEHYDE |
| D-LIMONENE | 5.00% | TERPENE |
| PEONILE | 2.50% | NITRILE |
| ETHYLENE BRASSYLATE | 12.50% | ESTER |
| PHENOXANOL | 2.50% | ALCOHOL |

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of liquid detergent added to 99 grams of water, then filtered through Whatman 597 filter catalog number 10311808) is added powder or slurry that achieves a concentration of approximately 1 wt. % perfume oil in the detergent solution. For water solubility, the powder is simply dosed into water rather than detergent solution. For the Detergent Dissolution Test, the sample is mixed at 200 RPM for 30 minutes at 33.3° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are two techniques utilized to evaluate odor of fabrics:

1) The dried fabrics from the Detergent Dissolution Test+Fabric Preparation test are evaluated olfactively by a panel before and after rubbing. A subjective grading scale is used to grade fabrics before rubbing and after rubbing. In the case of before rubbing, the control that is used is a fabric treated with neat fragrance oil in the detergent solution. In the case of rubbed fabric, the control is the fabric before rubbing is performed.

TABLE 2

Odor grading scale

| Odor Grade | Description |
| --- | --- |
| 0 | No Difference vs. Control |
| 1 | Slight Difference vs. Control |
| 2 | Noticeable Difference vs. Control (detectable difference) |
| 3 | Significant difference vs. control (high intensity vs. control) |
| 4 | Very High Intensity Bloom vs. control |
| 5 | Extremely High Intensity vs. Control |

The dried fabrics from the Detergent Dissolution Test+ Fabric Preparation test are evaluated by an Odor Meter (Shinyei Technology model OMX-SRM) before and after rubbing. This method reports the total concentration of volatiles in the headspace and is reported in milligrams per cubic meter as a function of time.

Free Oil

Approximately 0.20 grams to 0.27 grams of microcapsule slurry is preweighed in a 20 mL glass scintillation vial. 10 mL of hexane is added to the slurry. The scintillation vial is overturned 10 times to allow for mixing. The scintillation vial is then placed on a platform shaker that shakes the vial at a frequency of 1/sec to allow for mixing of the contents, for 10 minutes. The scintillation vial is allowed to sit unagitated at room temperature for 10 minutes. Sodium sulfate or sodium chloride could be added if there is a lack of phase separation of the hexane layer observed. Approximately 3 mL of the clear hexane layer is removed, placed into a syringe filter (0.45 micron, 25 mm diameter Acrodisc PTFE filter), and decanted into a GC vial. The sample is analyzed by Gas Chromatography. GC conditions are shown in Table 3 below.

TABLE 3

GC CONDITIONS

Oven

Initial Temperature: 40° C.
Rate: 5° C./min to 250° C.
Hold Time at Inlet Temp: 2 minutes
Run Time: 44.00 minutes
Inlet Mode: Split
Split Ratio: 8:1
Initial Temperature: 240° C.
Column Flow: 1.2 mL/min (constant flow mode)
Column Type: DB-5, 30 m, 0.25 mm diameter, 0.25 µm film thickness TABLE 3-continued

GC CONDITIONS

Basic MSD Settings

Low Mass: 50
High Mass: 550
Threshold: 500
MS Quad Temperature: 150° C.
MS Source Temperature: 230° C.
Transfer Line Temperature: 250° C.

Biodegradability

Biodegradability testing is carried out according to protocol OECD 301D. The microcapsule membrane is isolated by going through the following steps: (1) dilute the microcapsule slurry 1:10 with water, (2) centrifuge the slurry at 5000 RPM to isolate the capsules and remove all water soluble materials, (3) repeat these steps 3 times, (4) dry the isolated capsules in the oven at 105 degrees Centigrade for 1 hour, (5) mill the powder using ceramic beads, (6) vacuum dry the powder to remove residual oil at 0.3 torr for 1 day, (7) repeat milling of the powder using ceramic beads, (8) vacuum dry the powder to remove residual oil at 0.3 torr for 1 day, (9) repeat milling of the powder using ceramic beads, (10) vacuum dry the powder to remove residual oil at 0.3 torr for 1 day. In order to assure that residual oil has been removed, perform hexane extraction followed by Gas Chromatography analysis on the dried powder to assure less than 5% residual oil. Thermal Gravimetric Analysis (TGA) can also be used to verify less than 5% residual oil, when comparing to the TGA profile of the neat oil. However, TGA is less exact since polymer degradation could also occur as a result of heating.

The isolated polymer is then subjected to OECD 301D protocol, available at https://www.oecd.org/chemicalsafety/ risk-assessment/1948209.pdf, with the following experimental conditions:

1) test substance concentration in the mineral medium is 5 mg/L 2) 300 mL BOD bottles with glass stoppers are used 3) An incubator at 20 C is used to age the samples in the dark 4) The mineral stock solutions as provided in the method are prepared 5) The inoculum comprises Interlab Polyseed seed BOD inoculum tablets. Such tablets are EPA accepted, non-pathogenic, free of nitrifying microorganisms. 1 capsule is mixed with 0.5 L of APHA standard dilution water at 20 C, and stirred for 60 minutes.

6) COD of the isolated polymer is measured using Hach kit

The bottles are checked for dissolved oxygen at 0 days, 28 days, and 60 days. Intermittent points can also be taken since an asymptotic value may be reached much sooner than 60 days. The percent degradation is analyzed via the calculations taught in the OECD 301D method.

Comparative Example 1

Polyacrylate and Polyurea Hybrid Capsule

The following capsules are prepared by free radical polymerization of acrylate monomers in situ with polyisocyanate-amine reaction to yield a hybrid organic wall. High temperature is required to make a membrane. The membrane does not have any additional coatings to provide enhanced barrier properties of the present invention.

Prepare Oil Phase: mix 60 g of Perfume oil, 1.18 g of urethane acrylate oligomer, 2.36 g of aromatic acid acrylate half ester, 5.16.3 g of polyisocyanate and 0.34 g of Vazo-68 respectively. Contents of the mixture are allowed to stir at room temperature using a magnetic stir bar at 100-150 rpm for 20 minutes.

Prepare Aqueous Phase: 210 grams of 5 wt. % aqueous solution of polyvinyl pyrrolidone is prepared Emulsion Formation: The prepared oil phase is added into the aqueous phase while agitating the aqueous phase using a Caframo BDC6015, 4-blade pitched agitator shaft 1" diameter, at 750 rpm for 25 minutes to form a premix emulsion. An aliquot is analyzed by optical microscopy to understand particle size of the emulsion. 2 grams of water borne silsesquioxane oligomer is added dropwise and the reaction mixture is allowed to stir for next 5 hr at room temperature. The reaction mixture is then heated to 85° C. for 4 hours, followed by overnight stirring while cooling the batch.

Example 1. Type A Particles

Prepare Oil Phase: 53 g of Perfume oil, 1.83 g of sorbitol polyglycidyl ether, 00.64 gg of Trimethylolpropane triglycidyl ether, 1.01 g of Tetraethyl orthosilicate, 0.62 g of 1,2-Bis(Triethoxysilyl)ethane, 1.72 g of polyisocyanate and 2.9 g of isocyanurate based trimer of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 740 rpm for 20 minutes to form a pre-mix emulsion. An aliquot is analyzed by optical microscopy to understand particle size of the emulsion. Once the desired particle size is achieved a premixed solution of water borne silsesquioxane oligomer (1.5 g) is added dropwise. Continue to stir the contents for the next 2 hr followed by heating to 60° C. for next 4 hr. Allow the contents to stir overnight at above mentioned agitation rate to gradually cool emulsion slurry to room temperature.

Example 2. Type A Particles with Modified Cellulose

Prepare Oil Phase: 53 g of Perfume oil, 1.83 g of diepoxy of aliphatic dimer acid, 0.72 g of Trimethylolpropoane triglycidyl ether, 1.06 g of Tetraethyl orthosilicate, 0.62 g of 1,2-Bis(Triethoxysilyl)ethane, 0.9 g of Hydroxy propyl methyl cellulose, 1.73 g of polyisocyanate and 3 g of pentane-1,5-diisocyanate were added respectively and stirred for 10 minutes at 100-150 rpm using a magnetic stir bar for homogeneity.

Prepare Aqueous Phase: 125 g of 5 wt % aqueous solution of polyvinyl pyrrolidone is prepared.

Emulsion Formation: As explained in Example 1, oil phase is added to pre-mix aqueous phase stirring at rate of 830 rpm. Similar to example 1, after 20 minutes, a mixture of (1.65 g) water borne silsesquioxane oligomer, is added dropwise. Emulsion was stirred for 2 hr at room temperature followed by 4 hr at 60° C. Later contents were allowed to stir overnight to gradually cool the internal temperature of slurry to 23° C.

Example 3. Type A Particles With Inorganic Solid Particles

Prepare Oil Phase: 53 g of Perfume oil, 1.91 g of diepoxy of aliphatic dimer acid, 0.65 g of Trimethylolpropane triglycidyl ether, 1.20 g of Tetraethyl orthosilicate, 0.65 g of 1,2-Bis(Triethoxysilyl)ethane, 0.4 g of Talc, 1.81 g of polyisocyanate and 3.02 g of pentane-1,5-diisocyanate were added respectively and stirred for 10 minutes at 100-150 rpm using a magnetic stir bar for homogeneity.

Prepare Aqueous Phase: 125 g of 5 wt % aqueous solution of polyvinyl pyrrolidone is prepared.

Emulsion Formation: Following general procedure in Example 1, oil phase is added to prepared aqueous phase agitating at 800 rpm. As explained in Example 1, after 20 minutes, a mixture of 1.65 g 0.87 g water borne silsesquioxane oligomer, is added dropwise and contents are allowed to stir for 4 hr at room temperature. and later, mixture is heated to 60° C. for 4 hr followed by overnight cooling to room temperature.

Example 4 Type A Particles with Modified Polysaccharide

Prepare Oil Phase: 53 g of Perfume oil, 1.83 g of diepoxy of dimer acid, 0.67 g of Trimethylolpropane triglycidyl ether, 1.26 g of Tetraethyl orthosilicate, 0.72 g of 1,2-Bis (Triethoxysilyl)ethane, 1.83 g of polyisocyanate and 2.87 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 830 rpm for 20 minutes to form a pre-mix emulsion. An aliquot is analyzed by optical microscopy to understand particle size of the emulsion. Once the desired particle size is achieved a premixed solution of water borne silsesquioxane oligomer (0.51 g), Carboxymethyl chitosan (0.9 g) is added dropwise. Continue to stir the contents for the next 2 hr followed by heating to 60° C. for next 4 hr. Allow the contents to stir overnight at above mentioned agitation rate to gradually cool emulsion slurry to room temperature.

Example 5 Type A Particles with Polysaccharide

Prepare Oil Phase: 53 g of Perfume oil, 1.81 g of diepoxy of dimeric acid0.81 g of Trimethyolpropane triglycidyl ether, 1.23 g of Tetraethyl orthosilicate, 0.68 g of 1,2-Bis (Triethoxysilyl)ethane, 0.92 g of Tapioca starch, 1.81 g of polyisocyanate and 2.87 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 830 rpm for 20 minutes to form a pre-mix emulsion. An aliquot is analyzed by optical microscopy to understand particle size of the emulsion. Once the desired particle size is achieved a premixed solution of water borne silsesquioxane oligomer (1.58 g), is added dropwise. Continue to stir the contents for the next 2 hr followed by heating to 60° C. for next 4 hr. Allow the contents to stir overnight at above mentioned agitation rate to gradually cool emulsion slurry to room temperature.

Example 6. Type A Particles with Inorganic Solid Particles and Polyamide

Prepare Oil Phase: 53 g of Perfume oil, 1.76 g of diepoxy of dimeric acid, 0.68 g of Trimethylolpropane triglycidyl ether, 1.28 g of Tetraethyl orthosilicate, 0.69 g of 1,2-Bis (Triethoxysilyl)ethane, 0.7 g of Talc, 1.70 g of polyisocyanate and 2.85 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of Sokalan K9OP is prepared.

Emulsion Formation: The prepared oil phase is added into the aqueous phase while agitating the aqueous phase using a Caframo BDC6015, 3-blade pitched agitator shaft 1" diameter, at 830 rpm for 20 minutes to form a pre-mix emulsion. An aliquot is analyzed by optical microscopy to understand particle size of the emulsion. Once the desired particle size is achieved a premixed solution of water borne silsesquioxane oligomer (1.71 g), is added dropwise and contents are allowed to stir at room temperature for next 30 mins., Later an aqueous solution of isobutylene-maleic anhydride polymer (0.9 g) is added dropwise and the contents were set for heating to 60° C. for next 4 hr. Allow the contents to stir overnight at above mentioned agitation rate to gradually cool emulsion slurry to room temperature.

Example 7 Type B Particles with Inorganic Solid Particles

Prepare Oil Phase: 53 g of Perfume oil, 1.78 g of diepoxy of dimeric acid, 0.70 g of Trimethylolpropane triglycidyl ether, 1.19 g of Tetraethyl orthosilicate, 0.66 g of 1,2-Bis (Triethoxysilyl)ethane, 0.61 g of polyaziridine, 1.75 g of polyisocyanate and 2.91 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 830 rpm for 20 minutes to form a pre-mix emulsion. An aliquot is analyzed by optical microscopy to understand particle size of the emulsion. Once the desired particle size is achieved a premixed solution of water borne silsesquioxane oligomer (1.75 g), is added dropwise and contents are allowed to stir for the next 30 mins., at room temperature. Later, an aqueous solution of isobutylene-maleic anhydride polymer (0.9 g) is added dropwise and set to stir 1 hr at room temperature. Next, the slurry is acidified to pH (5.5) using aqueous 5% HCl and contents were set to heat to 60° C. for next 4 hr. Allow the contents to stir overnight at above mentioned agitation rate to gradually cool emulsion slurry to room temperature.

Example 8 Type B Particles with Modified Polysaccharide

Prepare Oil Phase: 53 g of Perfume oil, 1.79 g of diepoxy of dimeric acid, 0.66 g of Trimethylolpropane triglycidyl ether, 1.17 g of Tetramethyl orthosilicate, 0.67 g of 1,2-Bis(Triethoxysilyl)ethane, 0.7 g of Talc, 0.62 g of polyaziridine, 1.9 g of polyisocyanate and 3.42 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyinyl pyrrolidone is prepared.

Emulsion Formation: The prepared oil phase is added into the aqueous phase while agitating the aqueous phase using a Caframo BDC6015, 3-blade pitched agitator shaft 1" diameter, at 750 rpm for 20 minutes to form a pre-mix emulsion. An aliquot is analyzed by optical microscopy to understand particle size of the emulsion. Once the desired particle size is achieved a premixed solution of water borne silsesquioxane oligomer (2 g), is added dropwise and set forth to stir for next 30 mins., at room temperature. Later, an aqueous solution of isobutylene-maleic anhydride (0.9 g) is added to the slurry dropwise. After 20 mins., of stirring, solid carboxymethyl starch (0.9 g) is added and the contents were acidified with aqueous 5% HCl, followed by heating the contents to 60° C. for next 4 hr. Allow the contents to stir overnight at above mentioned agitation rate to gradually cool emulsion slurry to room temperature.

Example 9 Type A Particles with Catalyst

Prepare Oil Phase: 45 g of Perfume oil, 1.42 g of sorbitol polyglycidyl ether, 0.75 g of Trimethylolpropane triglycidyl ether, 1.17 g of Tetraethyl orthosilicate, 0.6 g of 1,2-Bis (Triethoxysilyl)ethane, 1.34 g of polyisocyanate, and 2.15 g of pentane-1,5-diisocyanate were mixed in the order mentioned. Contents were allowed to stir for 10 minutes at 100-150 rpm using a magnetic stir bar for homogeneity.

Prepare Aqueous Phase: 125 grams of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 830 rpm for 20 minutes to form a pre-mix emulsion. An aliquot is analyzed by optical microscopy to understand particle size of the emulsion. Once the desired particle size is achieved a premixed solution of water borne silsesquioxane oligomer (1.15 g), and catalytic amount of pentaethylene hexamine (0.2 g) is added dropwise. Continue to stir the contents for the next 2 hr followed by heating to 60° C. for next 4 hr. Allow the contents to stir overnight at above mentioned agitation rate to gradually cool emulsion slurry to room temperature.

Example 10 Type C Particles With Modified Polysaccharide Coating

Prepare Oil Phase: 53 g of Perfume oil, 1.64 g of sorbitol polyglycidyl ether, 0.69 g of Trimethylolpropane triglycidyl ether, 1.28 g of Tetraethyl orthosilicate, 0.6 g of 1,2-Bis (Triethoxysilyl)ethane, 1.78 g of polyisocyanate and 3.2 g of pentane-1,5-diisocyanate were mixed in the order mentioned. Contents were allowed to stir for 10 minutes at 100-150 rpm using a magnetic stir bar for homogeneity.

Prepare Aqueous Phase: 125 g of 5 wt % aqueous solution of polyvinyl pyrrolidone is prepared.

Emulsion Formation: The prepared oil phase is added into the aqueous phase while agitating the aqueous phase using a Caframo BDC6015, 3-blade pitched agitator shaft 1" diameter, at 775 rpm for 20 minutes to form a pre-mix emulsion. Once the desired particle size is achieved a pre-mixed solution of water borne silsesquioxane oligomer (1.25 g) is added dropwise and set forth to stir for additional 30 minutes at room temperature. Later an aqueous solution of isobutylene-maleic anhydride co-polymer (0.9 g) is added dropwise and the contents are stirred at room temperature for additional 1 hour. Next, carboxymethyl starch (0.6 g) is added in small portions as solid to the slurry and pH of the slurry is made alkaline with 5% aqueous NaOH. A dropwise addition of 1,7-dibromohexane (1.5 g) is performed followed by heating the slurry to 60° C. for next 4 hours with continued stirring overnight to undergo gradual cooling to room temperature.

Example 11. Leakage Stability and Performance Testing

Microcapsules slurries are formulated into liquid detergent (PUREX FREE & CLEAR), to deliver approximately 0.3 wt % fragrance usage level in the liquid suspension, via the microcapsules or neat perfume oil. These samples are used for leakage stability testing. Equivalent samples are made with 0.5 wt % fragrance usage level in the suspension. Both mixtures are aged for 1 week at 40° C. After ageing, several tests are performed to evaluate the behavior of the capsules 1) Optical microscopy to observe capsule deflation
2) Approximately 5 grams of the detergent mixture is diluted with 5 grams of water to yield a dilute detergent solution containing approximately 0.15 wt % fragrance oil. This diluted suspension is mixed for 30 minutes at a temperature of 33 C at 250 RPM using a magnetic stirrer. Next, approximately 2 mL of the mixed solution is filtered through a black fabric, and allowed to dry overnight. The fabric odor intensity before rubbing and after rubbing is noted.
3) Laundry performance testing is performed with samples containing 0.5 wt % fragrance oil. Approximately 3.0 kg of fabrics are loaded into a Samsung front load washing machine consisting of 5 bath towels, 3 polycotton T-shirts, one 100% cotton t-shirt. No fabric softener or bleach is used. A cold wash is done (approximately 26 minute cycle time shown below). The fabrics are then dried in a Samsung machine dryer on hot cotton cycle for 45 minutes.

TABLE 4

Laundry cycle description

| Time Elapsed (min) | Cycle Description |
|---|---|
| 10 | Wash cycle ends |
| 4 | 1st Rinse Cycle |
| 3 | Spin Cycle |
| 4 | 2nd Rinse Cycle |
| 8 | Spin Cycle |
| 1 | slow spin, end of cycles |

Fabrics are graded before rub and after rub. The results of such testing is shown in the table below. The formulations according to this invention are able to survive the liquid laundry matrix (to retain perfume inside the capsule), are able to survive the dilution in the washing machine, are able to deposit onto the fabric, and are able to deliver a noticeable fragrance intensity on fabric, before and after rubbing the fabric. Such capsules are expected to provide fragrance longevity on laundered fabrics.

TABLE 5

Fabric odor performance of microcapsule slurries aged in liquid detergent for 1 week at 40° C.

| Material/Attribute | A | B | C | D | E | F | H | I | J | K | L | M | N |
|---|---|---|---|---|---|---|---|---|---|---|---|---|---|
| Liquid Detergent | 0 | 50.11 | 50.03 | 50.1 | 0 | 0 | 0 | 0 | 50.03 | 0 | 50 | 50 | |
| Liquid Fabric Softener | 35.01 | 0 | 0 | 0 | 35 | 35 | 35 | 35 | 0 | 35 | 0 | | 35 |
| Example 1 | 0.438 | | | | | | | | | | | | |
| Example 2 | | 0.626 | | | | | | | | | | | |
| Example 3 | | | 0.625 | | | | | | | | | | |
| Example 4 | | | | 0.626 | | | | | | 0.438 | | | |
| Example 5 | | | | | 0.438 | | | | | | | | |
| Example 6 | | | | | | 0.438 | | | | | 0.625 | | |
| Example 7 | | | | | | | 0.438 | | | | | | |
| Example 8 | | | | | | | | 0.438 | | | | | |
| Example 9 | | | | | | | | | 0.625 | | | | |
| Comparative Capsule 1 | | | | | | | | | | | | 0.625 | 0.440 |
| Pre-Rub DFO - Det Diss | 0 | 0 | 3.5 | 1 | 3 | 3 | 3 | 3 | 0 | 3 | 3 | 0 | 0 |
| Post-Rub DFO - Det Diss | 4 | 4.5 | 4 | 5 | 5 | 5 | 5 | 5 | 4 | 4 | 5 | 3 | 1 |
| Pre-Rub DFO - Laundry | 1.25 | 0.9 | 1.3 | 1.2 | 1 | 0 | 2.3 | 2.4 | 1 | 0.7 | 1.2 | 0 | 0 |
| Post-Rub DFO - Laundry | 2.9 | 4.33 | 3.3 | 3.8 | 3.6 | 1.3 | 4.6 | 4 | 3 | 2 | 3 | 2 | 0 |

Example 12. Environmental Biodegradability

Microcapsules of various examples above were evaluated for environmental biodegradability by adapting the OCDE/OECD 301D Closed Bottle Test method, as described in the Biodegradability test method description.

TABLE 6

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dehydrate | $Na_2HPO_4$—$2H_2O$ | 33.40 |
| | Ammonium chloride | $NH_4Cl$ | 0.50 |
| | Dissolve in water and bring to 1 L. pH to 7.4 | | |

TABLE 6-continued

Mineral Oil Solutions

| Mineral Solution ID | Ingredient | Formula | Mass (g) |
|---|---|---|---|
| B | Calcium Chloride anhydrous OR | $CaCl_2$ | 27.50 |
|  | Calcium Chloride dehydrate Dissolve in water and bring to 1 L. | $CaCl_2-2H_2O$ | 36.40 |
| C | Magnesium sulfate heptahydrate Dissolve in water and bring to 1 L. | $MgSO_4-7H_2O$ | 22.50 |
| D | Iron (III) chloride hexahydrate Dissolve in water and bring to 1 L. | $FeCl_3-6H_2O$ | 0.25 |

To 996 mL of the APHA standard dilution water is added 2 polyseed BOD tablets, followed by addition of 1 mL each of mineral solutions A, B, C, and D. Prepare approximately 300 mL solutions containing the particles to be tested (approximately 1.5 milligrams of the isolated polymer is added to each BOD bottle). Fill BOD bottles (300 mL capacity) just past the neck of the bottle. Insert stopper. Store BOD bottles in the dark in an incubator maintained at 20 degrees Centigrade. Use dissolved oxygen meter (YSI 5000), and YSI5905 Dissolved Oxygen meter probe to measure oxygen at specific time points.

The dissolved oxygen measured values as a function of time, and the calculation methods presented in OECD 301D method are utilized to calculate the % biodegradability. The Environmental Biodegradability index is calculated by multiplying the measured % biodegradability by 100. The results are listed in Table 7 below.

TABLE 7

Environmental Biodegradability Results

| Material/Attribute | OECD 301D % Biodegradability (60 day) | Biodegradability Index |
|---|---|---|
| Example 1 | 65% | 65 |
| Example 2 | 65% | 65 |
| Example 3 | 73% | 73 |
| Example 6 | 63% | 63 |
| Example 7 | 68% | 68 |
| Example 8 | 75% | 75 |
| Example 9 | 90% | 90 |
| Comparative Capsule 1 | 20% | 20 |

A biodegradability index greater than 60 meets current ECHA requirements for microplastics biodegradability (2019).

Example 13—Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of Examples 1 to 9, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 13.1 below.

TABLE 13.1

Hair Condition Formulation

| Components | Ex. I (LOT) (%) |
|---|---|
| Premix |  |
| Aminosilicone | — |
| PDMS | 1.0-1.5 |
| Gel matrix carrier |  |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers |  |
| Hydroxyethylcellulose (HEC) | 0.15-0.50 |
| PEG-2M (Polyox WAR N-10) | 0.30-0.60 |
| Others |  |
| Preservatives | 0.40-0.60 |

Example 14—Shampoo

Selected microcapsules from the above examples are formulated into a rinse-off shampoo formulation as follows: to 90.0 grams of shampoo formulation is added an appropriate amount of microcapsule slurry of Examples 1 to 9, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 14.1, 14.2 and 14.3 below.

TABLE 14.1

Shampoo Formulations of Examples 14A-14C.

| Ingredient | Example 14A | 14B | 14C |
|---|---|---|---|
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine 7 | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsules | 1.2 | 1.2 | 1.2 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW - 500,000, CD = 0.7, supplier Rhodia
[3] Mirapol 100S, 31.5% active, supplier Rhodia
4 Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 14.2

Shampoo Formulations of Examples 14D-14F.

| Ingredient | 14D | 14E | 14F |
|---|---|---|---|
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.2 | 1.2 | 1.2 |

[1] Glycidol Silicone
[4] Cyclopentasiloxane: SF1202 available from Momentive Performance Chemicals
[5] Behenyl trimethyl ammonium chloride/Isopropyl alcohol: Genamin™ KMP available from Clariant
[6] Cetyl alcohol: Konol™ series available from Shin Nihon Rika
[7] Stearyl alcohol: Konol™ series available from Shin Nihon Rika
[8] Methylchloroisothiazolinone/Methylisothiazolinone: Kathon™ CG available from Rohm & Haas
[9] Panthenol: Available from Roche
[10] Panthenyl ethyl ether: Available from Roche

TABLE 14.3

Shampoo Formulations of Examples 14G and 14H

| Ingredient | 14G | 14H |
|---|---|---|
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride [1] | 0.40 | |
| Guar Hydroxypropyl trimonium chloride [2] | | 0.40 |
| Dimethicone [3] | 2.00 | 2.00 |
| Gel Network [4] | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

[1] Jaguar C17 available from Rhodia
[2] N-Hance 3269 (with Mol. W. of ~500,000 and 0.8 meq/g) available from Aqualon/Hercules
[3] Viscasil 330M available from General Electric Silicones
[4] Gel Networks; See composition in Table 14.4 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 14.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 15—Lotion

For the examples shown in Table 15 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each phase reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 15

Lotion Formulations (Examples 15A-15C).

| Ingredient/Property | 15A | 15B | 15C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO$_2$ | | | 0.50 |
| Iron oxide coated Mica | | | 0.65 |
| TiO$_2$ Coated Mica | 1.00 | 1.00 | |
| Fragrance Microcapsules | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would deemed suitable by one of skill in the art.

Example 16—Antiperspirant/Deodorant

Example 16A of Table 16.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container and allowed to solidify and cool to ambient temperature.

TABLE 16.1

Antiperspirant/Deodorant Formulation (Example 16A).

| Ingredient | Example 16A |
|---|---|
| Part I: Partial Continuous Phase | |
| Hexamethyldisiloxane[1] | QS |
| DC5200[2] | 1.20 |
| Fragrance | 0.35 |
| Fragrance Capsules | 1.00 |
| Part II: Disperse Phase | |
| ACH (40% solution)[4] | 40.00 |
| propylene glycol | 5.00 |
| Water | 12.30 |
| Part III: Structurant Plus Remainder of Continuous Phase | |
| FINSOLVE TN | 6.50 |

QS—indicates that this material is used to bring the total to 100%
[1]DC 246 fluid from Dow Corning
[2]from Dow Corning
3 Standard aluminum chlorohydrate solution Examples 16B to 16E of Table 16.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 16F of Table 16.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally, an appropriate actuator is connected to the valve to allow dispensing of the product.

TABLE 16.2

Antiperspirant/Deodorant Formulations

| | Example | | | | |
|---|---|---|---|---|---|
| Ingredient | 16B | 16C | 16D | 16E | 16F |
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG -8 | | | | 20 | |
| ethanol | | | | | QS |
| Water | QS | QS | QS | QS | |

TABLE 16.2-continued

Antiperspirant/Deodorant Formulations

| | Example | | | | |
|---|---|---|---|---|---|
| Ingredient | 16B | 16C | 16D | 16E | 16F |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragrance | 0.5 | 0.5 | 0.5 | 0.5 | 0.5 |
| Fragrance capsules | 1.0 | 1.0 | 1.0 | 1.0 | 0.5 |
| Propellant (1,1 difluoroethane) | | | | | 40 |

QS—indicates that this material is used to bring the total to 100%.

Example 17—Rinse-off Conditioner

The conditioning compositions of Examples 17A through 17F of Table 17 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 17B of Table 17 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 20

Rinse-Off Conditioner Formulations (Examples 17A-17F).

| | Example | | | | | |
|---|---|---|---|---|---|---|
| Ingredient | 17A | 17B | 17C | 17D | 17E | 17F[3] |
| Premix | | | | | | |
| Aminosilicone-1 [1] | 0.50 | 0.50 | | | | |
| Aminosilicone-2 [2] | | | 0.50 | 0.50 | 0.50 | |
| PDMS | | | | | | 0.50 |
| Fragrance microcapsules | ... | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 m mol/g and a viscosity of 3,000-8,000 mPa · s, which is water insoluble
[2] Aminosilicone-2 (TAS): having an amine content of 0.04-0.06 m mol/g and a viscosity of 10,000-16,000 mPa · s, which is water insoluble
[3]Comparative example with PDMS instead of amino silicone Example 18—Body Cleansing Composition The body cleaning compositions of Examples 18A-18C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The Benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 18

Body Cleansing Composition Formulations (Examples 18A-18C).

| Ingredient | 18A | 18B | 18C |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aquaion) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules | 10 | 10 | 10 |
| III: Surfactant Phase:Benefit Phase Blending Ratio | 50:50 | 90:10 | 90:10 |

Example 19—Fabric Softening Product

Non-limiting examples of product formulations containing purified perfume microcapsules of the aforementioned examples are summarized in the following table.

TABLE 19

Fabric Softening Product Formulations (Examples 19A-19J).

| Ingredient | 19A | 19B | 19C | 19D | 19E | 19F | 19G | 19H | 19I | 19J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON CG available from Rohm and Haas Co. "PPM" is "parts per million."
[j] Gluteraldehyde
[k] Silicone antifoam agent available from Dow Corning Corp, under the trade name DC2310.
[l] Hydrophobically-modified ethoxylated urethane available from Rohm and Haas under the tradename Aculyn™ 44.
*Suitable microcapsules provided in Examples 1 to 9. (Percent active relates to the core content of the microcapsule)

Example 20—Dry Laundry Formulations

Non-limiting examples of product formulations containing purified perfume microcapsules of the aforementioned examples are summarized in the following table.

TABLE 20

Dry Laundry Formulations (Examples 20A-20G)

| Ingredient | 20A | 20B | 20C | 20D | 20E | 20F | 20G |
|---|---|---|---|---|---|---|---|
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxy ethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Examples 1 to 9) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS—as used herein indicates that this material is used to bring the total to 100%.

Example 21—Liquid Laundry Formulations (HDLs)

Non-limiting examples of product formulations containing purified perfume microcapsules of the aforementioned examples are summarized in Tables 21.1, 21.2 and 21.3 below.

TABLE 21.1

Liquid Laundry Formulations (HDLs)

| Ingredient | 21A | 21B | 21C | 21D | 21E | 21F |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |

TABLE 21.1-continued

Liquid Laundry Formulations (HDLs)

| Ingredient | 21A | 21B | 21C | 21D | 21E | 21F |
|---|---|---|---|---|---|---|
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (di sulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules of Examples 1 to 9 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 21.2

Liquid Laundry Detergent Formulations

| Ingredient | 21G | 21H | 21I | 21J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |
| Bentonite Softening Clay | | 1.0 | | |
| Polyquaternium 10 - Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | 1.0 | |
| Perfume micro capsules (expressed as perfume oil) of Example 1 to 9 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 21.3

Liquid Laundry Detergent Formulations.

| Ingredient | 21K | 21L | 21M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |

TABLE 21.3-continued

Liquid Laundry Detergent Formulations.

| Ingredient | 21K | 21L | 21M |
|---|---|---|---|
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Examples 1 to 9 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 22—Liquid and Gel Detergents

Non-limiting examples of product formulations containing purified perfume microcapsules of the aforementioned examples are summarized in Table 22 below.

TABLE 22

Liquid and Gel Detergent Formulations (% by Weight)

| Ingredient | 22A | 22B | 22C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Examples 1 to 9 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

Example 23—Liquid Unit Dose

The following are examples of unit dosage forms wherein the liquid composition is enclosed within a PVA film. The preferred film used in the present examples is Monosol M8630 76 μm thickness.

TABLE 23

Unit Dose Laundry Cleaner

| | 23A 3 compartments | | | 23B 2 compartments | | 23C 3 compartments | | |
|---|---|---|---|---|---|---|---|---|
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |

TABLE 23-continued

| | Unit Dose Laundry Cleaner | | | | | | | |
|---|---|---|---|---|---|---|---|---|
| | Example | | | | | | | |
| | 23A 3 compartments | | | 23B 2 compartments | | 23C 3 compartments | | |
| | Compartment # | | | | | | | |
| | 42 | 43 | 44 | 45 | 46 | 47 | 48 | 49 |
| | Dosage (g) | | | | | | | |
| | 34.0 | 3.5 | 3.5 | 30.0 | 5.0 | 25.0 | 1.5 | 4.0 |
| Ingredients | Weight % | | | | | | | |
| Polycarboxylate | | | | 1.0 | | | | |
| Ethoxylated Polyethylenimine[1] | 2.2 | 2.2 | 2.2 | | | | | |
| Hydroxy ethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Microcapsules Example 1 to 9 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine) [2] | To pH 8.0 for liquids To RA > 5.0 for powders | | | | | | | |
| Solvents (1,2 propanediol, ethanol), sodium sulfate | To 100 p | | | | | | | |

[1]Polyethylenimine (MW = 600) with 20 ethoxylate groups per —NH.
[2] RA = Reserve Alkalinity (g NaOH/dose)

While the invention has been described in detail and with reference to specific examples thereof, it will be apparent to one skilled in the art that various changes and modifications can be made therein without departing from the spirit and scope thereof.

What is claimed is:

1. A composition comprising a microcapsule formed under acidic conditions, the microcapsule comprising:
  (a) a core composition comprising at least one hydrophobic active ingredient and an unreacted amount of an epoxy, an epoxide curing agent, an isocyanate, and an organofunctional silane; and
  (b) a wall material surrounding a portion of the core composition, the wall material comprising:
    i. one or more of a first reaction product of a first reactant comprising an amine and a second reactant which is at least one member selected from the group consisting of the epoxy, the epoxide curing agent, the isocyanate, and the organofunctional silane; and
    ii. a second reaction product of the first reactant amine with a third reactant comprising a copolymer of maleic anhydride.

2. The composition of claim 1, wherein the second reaction product is further reacted with a fourth reactant selected from the group consisting of a polyaziridine, a polyoxazoline and a carbodiimide.

3. The composition of claim 1, wherein the wall material forms around the core in a one pot process.

4. The composition of claim 1, wherein the wall material further comprises an inorganic solid particle, a polysaccharide, or a plasticizer.

5. The composition of claim 1, wherein the microcapsule is effective to retain the at least one hydrophobic active ingredient upon exposure to water and effective to release the at least one hydrophobic active ingredient in response to friction.

6. The composition of claim 2, wherein the wall material comprises the first reaction product of the amine of the first reactant and the second reactant, and the second reaction product of the amine with the copolymer of maleic anhydride further reacted with the polyaziridine.

7. The composition of claim 1, wherein the amine is at least one member selected from the group consisting of: a liner aliphatic amine, an aromatic amine, a silicone amine, a branched amine, a polyamine, a polyetheramine, and an amino acid.

8. The composition of claim 1, wherein the isocyanate is at least one member selected from the group consisting of an aliphatic isocyanate, an aromatic isocyanate, a polymeric isocyanate, a cyclic isocyanate, a hydrophilic isocyanate, a hydrophobic isocyanate, a isocyanurate, a waterborne isocyanate and a urethane acrylate containing isocyanate functionalities.

9. The composition of claim 1, wherein the organofunctional silane is at least one member selected from the group consisting of: an alkoxylated silane, a trialkoxy silane, a functionalized trialkoxysilane, and a tetraalkoxylated silane.

10. The composition of claim 9, wherein the tetraalkoxylated silane is selected from the group consisting of a tetramethoxy silane and a tetraethoxy silane.

11. The composition of claim 1, wherein the epoxy is at least one member selected from the group consisting of: an epoxidized unsaturated oil, an epoxidized vegetable oil, an epoxidized alcohol and an epoxidized polysaccharide.

12. The composition of claim 1, wherein the epoxide curing agent is a low temperature curing agent having at least 2 epoxy functional groups which are terminally located selected from the group consisting of: a trimethylol propane triglycidyl ether, a resin containing acrylate and epoxy functional groups, a diepoxide of a cycloapliphatic alcohol, a hydrogenated Bisphenol A, and a resorcinol/bisphenol F resin with polyfunctional epoxide resin blend.

13. The composition of claim 1, wherein the copolymer of maleic anhydride is at least one member selected from the group consisting of reaction products of dehydrated maleic acid with acyclic, cyclic or vinylic aromatic alkenes.

14. The composition of claim 4, wherein the polysaccharide is at least one member selected from the group consisting of: a natural starch, a carboxy modified polysaccharide and a carboxy modified cellulose.

15. The composition of claim 14, wherein the polysaccharide comprises a carboxymethyl starch, a carboxymethyl chitosan, a chitosan oligosaccharide, a hydroxy propyl methyl starch, a hydroxy propyl cellulose, an ethyl cellulose, a methyl cellulose, or a octenyl succinic anhydride modified starch.

16. The composition of claim 4, wherein the inorganic solid particle is at least one member selected from organically modified or water insoluble clays, minerals, and salts.

17. The composition of claim 4, wherein the plasticizer has a molecular weight greater than 1000 Daltons, and is selected from the group consisting of methyl esters of rosin, polyazelate esters, di-fatty acid esters, citrate esters, polyadipate esters, and polyester resins consisting of inner and intra-esters of polyhydroxy carboxylic acids.

18. The composition of claim 1, wherein the microcapsule has a diameter from 0.1 microns to less than 200 microns.

19. The composition of claim 2, wherein the polyaziridine is a polymer with more than one aziridine functionality present as terminal groups of a monomer or oligomer.

20. The composition of claim 2, wherein the polyoxazoline is a polymer with more than one oxazoline functional group present as terminal ends of a polymer or as pendant groups attached to a polymer backbone.

21. The composition of claim 2, wherein the carbodiimide is at least one member selected from the group consisting of: a waterborne polycarbodiimide resin, a copolymer containing carbodiimide and isocyanate functionalities, a copolymer containing carbodiimide and epoxy functionalities, and an ethyl carbodiimide hydrochloride.

22. The composition of claim 2, wherein the wall material has an environmental biodegradability of greater than 50%.

23. A method for preparing the composition of claim 1 comprising the microcapsule, said method comprising the steps of:
   (a) preparing an oil phase comprising at least one hydrophobic active ingredient, a isocyanate, an epoxy, a organofunctional silane, an epoxide curing agent, a polyaziridine, optionally a polysaccharide, optionally a plasticizer; and optionally an inorganic solid particle;
   (b) preparing an aqueous phase comprising an emulsifier;
   (c) combining the oil phase and the aqueous phase to emulsify the at least one hydrophobic active ingredient to provide an aqueous suspension of the at least one hydrophobic active ingredient;
   (d) adding an amine to react with the isocyanate, the epoxy, or the organofunctional silane for about 0.5 hours at room temperature;
   (e) adding a copolymer of maleic anhydride, predissolved in water and allow it to react with contents of the aqueous suspension for 1 hour;
   (f) acidifying the contents of the aqueous suspension by adding dilute hydrochloric acid or citric acid;
   (g) optionally, adding an acidified carboxy functional polysaccharide or cellulose to the aqueous suspension;
   (h) optionally, adding to the aqueous suspension a fresh aliquot of the polyaziridine or a polyoxazoline to enable crosslinking of the two free acids;
   (i) increasing the temperature to 60° C. and reacting for 2 to 5 hours; and
   (j) adding structuring agents to the aqueous suspension to homogeneously suspend the microcapsule in an aqueous dispersion.

24. The composition of claim 1, wherein the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the microcapsule in a water soluble film.

25. The method of claim 23, further comprising adding at least one suspension agent to suspend the microcapsule, wherein the at least one suspension agent is at least one member selected from the group consisting of a rheology modifier, a structurant and a thickener.

26. The composition of claim 24, further comprising at least one suspension agent to suspend the microcapsule, wherein the at least one suspension agent is at least one member selected from the group consisting of a rheology modifier, a structurant and a thickener.

27. The method of claim 23, wherein the emulsifier is a member selected from the group consisting of palmitamidopropyltrimonium chloride, distearyldimonium chloride, cetyltrimethylammonium chloride, quaternary ammonium compounds, fatty amines, aliphatic ammonium halides, alkyldimethyl benzylammonium halides, alkyldimethylethylammonium halides, polyethyleneimine, poly(-dimethylamino)ethyl methacrylate)methyl chloride quaternary salt, poly(l-vinylpyrrolidone-co-2-dimethylaminoethyl methacrylate), poly(acrylamide-co-diallyldimethylammonium chloride), poly(allylamine), polybis(2-chloroethyl)ether-alt-1,3-bis(3-(dimethylamino)propylurea quaternized, poly(dimethylamine-co-epichlorohydrin-co-ethylenediamine), polyalkylene glycol ether, polyvinyl acetate, copolymers of polyvinyl acetate, polyvinyl alcohol, polyacrylamide, poly(N-isopropylacrylamide), poly (2-hydroxypropyl methacrylate), poly(-ethyl-2-oxazoline), poly(2-isopropenyl-2-oxazoline-co-methyl methacrylate), poly(methyl vinyl ether), and polyvinyl alcohol-co-ethylene), polyvinyl pyrrolidone, copolymers of polyvinyl pyrrolidone, 1H-Imidazolium, 1-ethenyl-3-methyl-, chloride, polymer with 1-ethenyl-2-pyrrolidinone, vinyl acetate, hydroxypropyl methyl cellulose, and gum arabic.

28. The composition of claim 1, wherein the wall material is a single membrane layer.

* * * * *